(12) United States Patent
Nakazawa

(10) Patent No.: US 9,549,895 B2
(45) Date of Patent: Jan. 24, 2017

(54) METHODS AND COMPOSITIONS FOR PRESERVING THE VIABILITY OF PHOTORECEPTOR CELLS

(75) Inventor: Toru Nakazawa, Sendai Miyagi (JP)

(73) Assignee: Massachusetts Eye and Ear Infirmary, Boston, MA (US)

( * ) Notice: Subject to any disclaimer, the term of this patent is extended or adjusted under 35 U.S.C. 154(b) by 2571 days.

(21) Appl. No.: 11/587,022

(22) PCT Filed: Apr. 22, 2005

(86) PCT No.: PCT/US2005/013710
§ 371 (c)(1),
(2), (4) Date: Aug. 7, 2007

(87) PCT Pub. No.: WO2005/105133
PCT Pub. Date: Nov. 10, 2005

(65) Prior Publication Data
US 2007/0287756 A1    Dec. 13, 2007

Related U.S. Application Data

(60) Provisional application No. 60/564,717, filed on Apr. 23, 2004.

(51) Int. Cl.
A61K 47/00 (2006.01)
A61K 9/00 (2006.01)

(52) U.S. Cl.
CPC ................................ *A61K 9/0048* (2013.01)

(58) Field of Classification Search
CPC ................................................... A61K 9/0048
See application file for complete search history.

(56) References Cited

U.S. PATENT DOCUMENTS

| | | |
|---|---|---|
| 5,443,505 A | 8/1995 | Wong et al. |
| 5,667,968 A | 9/1997 | LaVail et al. |
| 5,766,242 A | 6/1998 | Wong et al. |
| 5,767,079 A | 6/1998 | Glaser et al. |
| 5,837,817 A | 11/1998 | Aggarwal et al. |
| 5,840,719 A | 11/1998 | Rubin et al. |
| 6,117,675 A | 9/2000 | van der Kooy et al. |
| 6,251,090 B1 | 6/2001 | Avery et al. |
| 6,299,895 B1 | 10/2001 | Hammang et al. |
| 6,331,523 B1 | 12/2001 | Kljavin et al. |
| 6,375,972 B1 | 4/2002 | Guo et al. |
| 6,378,526 B1 | 4/2002 | Bowman et al. |
| 6,379,666 B1 * | 4/2002 | Tobinick .................... 424/134.1 |
| 6,397,849 B1 | 6/2002 | Bowman et al. |
| 6,413,540 B1 | 7/2002 | Yaacobi |
| 6,416,777 B1 | 7/2002 | Yaacobi |
| 6,531,128 B1 | 3/2003 | Wax et al. |
| 6,541,489 B1 | 4/2003 | Barta et al. |
| 6,750,196 B1 | 6/2004 | Reh et al. |
| 6,780,837 B1 | 8/2004 | LaVail et al. |
| 6,814,966 B1 | 11/2004 | Wax et al. |
| 6,815,418 B2 | 11/2004 | Twardzik et al. |
| 7,119,203 B2 | 10/2006 | Barta et al. |
| 7,592,330 B2 | 9/2009 | Grosskreutz |
| 7,811,832 B2 | 10/2010 | Zacks et al. |
| 2001/0026801 A1 | 10/2001 | Tobinick |
| 2004/0265392 A1 | 12/2004 | Tovar et al. |
| 2005/0032183 A1 | 2/2005 | Osslund et al. |
| 2005/0129684 A1 | 6/2005 | Zacks et al. |
| 2006/0079492 A1 | 4/2006 | Ahlem et al. |
| 2006/0134737 A1 | 6/2006 | Beyaert et al. |
| 2007/0032427 A1 | 2/2007 | Grosskreutz |
| 2010/0034808 A1 | 2/2010 | Nakazawa |
| 2010/0074882 A1 | 3/2010 | Grosskreutz |

FOREIGN PATENT DOCUMENTS

| | | |
|---|---|---|
| EP | 1717246 | 11/2006 |
| JP | 2001058950 | 3/2001 |
| WO | WO-9533051 | 12/1995 |
| WO | WO-9601642 | 1/1996 |
| WO | WO-9948495 | 9/1999 |
| WO | WO-0040089 | 7/2000 |

(Continued)

OTHER PUBLICATIONS

Aaberg TM. Does hyperoxygenation limit retinal degeneration after retinal detachment? *Am J Ophthalmol*. (1999) vol. 128(2):231.
Abu el-Asrar AM, Van Damme J, Put W, Veckeneer M, Dralands L, Billiau A, Missotten L. Monocyte chemotactic protein-1 in proliferative vitreoretinal disorders. *Am J Ophthalmol*. (1997) vol. 123(5):599-606.
Afford S and Randhawa S, Apoptosis, *J Clin Pathol: Mol Pathol* 2000; 53:55-63.
Anderson DH, Stern WH, Fisher SK, Erickson PA, and Borgula GA, Retinal detachment in the cat: the pigment epithelial-photoreceptor interface, *Investigative Ophthalmology & Visual Science* (1983), vol. 24, 906-926.
Baudouin C, Fredj-Reygrobellet D, Brignole F, Nègre F, Lapalus P, Gastaud P. Growth factors in vitreous and subretinal fluid cells from patients with proliferative vitreoretinopathy. Ophthalmic Res. (1993) vol. 25(1):52-59.
Borhani H, Peyman GA, Rahimy MH, Beuerman RW. Vitreoretinal toxicity of basic fibroblast growth factor. *Int Ophthalmol*. (1993) vol. 17(4):195-199.

(Continued)

*Primary Examiner* — Zohreh Fay
(74) *Attorney, Agent, or Firm* — Goodwin Procter LLP

(57) ABSTRACT

Provided are methods and compositions for maintaining the viability of photoreceptor cells following retinal detachment. The viability of photoreceptor cells can be preserved by administering a neuroprotective agent, for example, a substance capable of suppressing endogenous MCP-1, a MCP-1 antagonist, a substance capable of suppressing endogenous TNF-alpha, a TNF-alpha antagonist, a substance capable of suppressing endogenous IL-1 beta, an IL-1 beta antagonist, a substance capable of inducing endogenous bFGF, exogenous bFGF, a bFGF mimetic, and combinations thereof, to a mammal having an eye with retinal detachment. The neuroprotective agent maintains the viability of the photoreceptor cells until such time that the retina becomes reattached to the underlying retinal pigment epithelium and choroid. The treatment minimizes the loss of vision, which otherwise may occur as a result of retinal detachment.

18 Claims, 12 Drawing Sheets

(56) References Cited

FOREIGN PATENT DOCUMENTS

| WO | WO-0128474 | 4/2001 |
|----|------------|--------|
| WO | WO-0149321 | 7/2001 |
| WO | WO-0289767 | 11/2002 |
| WO | WO-03061519 | 7/2003 |

OTHER PUBLICATIONS

Bryckaert M, Guillonneau X, Hecquet C, Courtois Y and Mascarelli F, Both FGF1 and Bcl-x synthesis are necessary for the reduction of apoptosis in retinal pigmented epithelial cells by FGF2: role of the extracellular signal-regulated kinase 2, *Oncogene* (1999), vol. 18, No. 52: 7584-7593.

CafféAR, Söderpalm AK, Holmqvist I and van Veen T, A Combination of CNTF and BDNF Rescues rd Photoreceptors but Changes Rod Differentiation in the Presence of RPE in Retinal Explants, *Investigative Ophthalmology and Visual Science* (2001); vol. 42:275-282.

Capeans C, De Rojas MV, Lojo S, Salorio MS. C-C chemokines in the vitreous of patients with proliferative vitreoretinopathy and proliferative diabetic retinopathy. *Retina.* (1998) vol. 18(6):546-550.

Chen B, Jiand D, Huang P, Tang L. Relationship between IL-1 beta and TNF-alpha in subretinal fluids of rhegmatogenous retinal detachment with PVR, *Hunan Yi Ke Da Xue Xue Bao.* (1998) vol. 23(5):483-485.

Cook B, Lewis GP, Fisher SK and Adler R, Apoptotic photoreceptor degeneration in experimental retinal detachment, *Investigative Ophthalmology & Visual Science* (1995), vol. 36: 990-996.

Cuthbertson RA, Lang RA, Coghlan JP. Macrophage products IL-1 alpha, TNF alpha and bFGF may mediate multiple cytopathic effects in the developing eyes of GM-CSF transgenic mice. *Exp Eye Res.* (1990) vol. 51(3):335-344.

El-Ghrably IA, Dua HS, Orr GM, Fischer D, Tighe PJ. Intravitreal invading cells contribute to vitreal cytokine milieu in proliferative vitreoretinopathy. *Br J Ophthalmol.* (2001) vol. 85(4):461-470.

Franks WA, Limb GA, Stanford MR, Ogilvie J, Wolstencroft RA, Chignell AH, Dumonde DC. Cytokines in human intraocular inflammation. *Curr Eye Res.* (1992) vol. 11 Suppl:187-191.

Gao H, Hollyfield JG. Basic fibroblast growth factor in retinal development: differential levels of bFGF expression and content in normal and retinal degeneration (rd) mutant mice. *Dev Biol.* (1995) vol. 169(1):168-184.

Geller SF, Lewis GP, Fisher SK. FGFR1, signaling, and AP-1 expression after retinal detachment: reactive Müller and RPE cells. *Invest Ophthalmol Vis Sci.* (2001) vol. 42(6):1363-1369.

Hackett SF, Schoenfeld CL, Freund J, Gottsch JD, Bhargave S, Campochiaro PA. Neurotrophic factors, cytokines and stress increase expression of basic fibroblast growth factor in retinal pigmented epithelial cells. *Exp Eye Res.* (1997) vol. 64(6): 865-873.

Hagimura N, Iida T, Suto K, Kishi S, Persistent foveal retinal detachment after successful rhegmatogenous retinal detachment surgery, *American Journal of Ophthalmology* (2002), 133: 516-520.

Hisatomi T, Sakamoto T, Goto Y, Yamanaka I, Oshima Y, Hata Y, Ishibashi T, Inomata H, Susin SA, Kroemer G. Critical role of photoreceptor apoptosis in functional damage after retinal detachment. *Curr Eye Res.* (2002) vol. 24(3):161-172.

Hisatomi T, Sakamoto T, Murata T, Yamanaka I, Oshima Y, Hata Y, Ishibashi T, Inomata H, Susin SA, Kroemer G. Relocalization of apoptosis-inducing factor in photoreceptor apoptosis induced by retinal detachment in vivo. *Am J Pathol.* (2001) vol. 158(4):1271-1278.

Itaya H, Hayashi A, Usui S, Hosohata J, Takahashi T, Fujikado T, Tano Y. Basic fibroblast growth factor inhibits choriocapillaris atrophy in rabbit. *Am J Ophthalmol.* (2001) vol. 132(1):94-100.

Ambati J, Gragoudas ES, Miller JW, You TT, Miyamoto K, Delori FC, and Adamis AP, Transscleral Delivery of Bioactive Protein to the Choroid and Retina, *Investigative Ophthalmology & Visual Science* (2000), vol. 41: 1186-1191.

Ambati J, Canakis CS, Miller JW, Gragoudas ES, Edwards A, Weissgold DJ, Kim I, Delori FC, and Adamis AP, Diffusion of High Molecular Weight Compounds through Sclera, *Investigative Ophthalmology & Visual Science* (2000), vol. 41: 1181-1185.

Kon CH, Occleston NL, Aylward GW, Khaw PT. Expression of vitreous cytokines in proliferative vitreoretinopathy: a prospective study. *Invest Ophthalmol Vis Sci.* (1999) vol. 40(3):705-712.

La Heij EC, van de Waarenburg MP, Blaauwgeers HG, Kessels AG, Liem AT, Theunissen C, Steinbusch H, Hendrikse F. Basic fibroblast growth factor, glutamine synthetase, and interleukin-6 in vitreous fluid from eyes with retinal detachment complicated by proliferative vitreoretinothy. *Am J Ophthalmol.* (2002) vol. 134(3):367-375.

La Heij EC, Van De Waarenburg MP, Blaauwgeers HG, Kessels AG, De Vente J, Liem AT, Steinbusch H, Hendrikse F. Levels of basic fibroblast growth factor, glutamine synthetase, and interleukin-6 in subretinal fluid from patients with retinal detachment. *Am J Ophthalmol.* (2001) vol. 132(4):544-550.

LaVail MM, Yasumura D, Matthes MT, Lau-Villacorta C, Unoki K, Sung CH and Steinberg RH, Protection of mouse photoreceptors by survival factors in retinal degenerations, Investigative Ophthalmology & Visual Science (1998), vol. 39: 592-602.

Lewis GP, Linberg KA, Geller SF, Guerin CJ and Fisher SK, Effects of the neurotrophin brain-derived neurotrophic factor in an experimental model of retinal detachment, *Investigative Ophthalmology & Visual Science* (1999), vol. 40: 1530-1544.

Lewis G, Mervin K, Valter K, Maslim J, Kappel PJ, Stone J, Fisher S, Limiting the proliferation and reactivity of retinal Miler cells during experimental retinal detachment: the value of oxygen supplementation, *American Journal of Ophthalmology* (1999), 128: 165-172.

Limb GA, Hollifield RD, Webster L, Charteris DG, Chignell AH. Soluble TNF receptors in vitreoretinal proliferative disease. *Invest Ophthalmol Vis Sci.* (2001) vol. 42(7):1586-1591.

Limb GA, Little BC, Meager A, Ogilvie JA, Wolstencroft RA, Franks WA, Chignell AH, Dumonde DC. Cytokines in proliferative vitreoretinopathy. *Eye.* 1991;5 ( Pt 6):686-693.

Limb GA, Earley O, Jones SE, LeRoy F, Chignell AH, Dumonde DC. Expression of mRNA coding for TNF alpha, IL-1 beta and IL-6 by cells infiltrating retinal membranes. *Graefes Arch Clin Exp Ophthalmol.* (Nov. 1994) ;232(11):646-651.

Marc RE, Murry RF, Fisher SK, Linberg KA, and Lewis GP, Amino acid signatures in the detached cat retina, *Investigative Ophthalmology & Visual Science* (1998), vol. 39, 1694-1702.

David P. Martin, Akira Ito, Kazuhiko Horigome, Patricia A. Lampe, Eugene M. Johnson Jr. Biochemical characterization of programmed cell death in NGF-deprived sympathetic neurons, *Journal of Neurobiology* (1992), vol. 23 (9): 1205-1220.

Mervin K, Valter K, Maslim J, Lewis G, Fisher S, Stone J. Limiting photoreceptor death and deconstruction during experimental retinal detachment: the value of oxygen supplementation. *Am J Ophthalmol.* (1999) vol. 128(2):155-164.

Mitamura Y, Takeuchi S, Yamamoto S, Yamamoto T, Tsukahara I, Matsuda A, Tagawa Y, Mizue Y, Nishihira J. Monocyte chemotactic protein-1 levels in the vitreous of patients with proliferative vitreoretinopathy. *Jpn J Ophthalmol.* (2002) vol. 46(2):218-221.

Ozaki S, Radeke MJ, Anderson DH. Rapid upregulation of fibroblast growth factor receptor 1 (flg) by rat photoreceptor cells after injury. *Invest Ophthalmol Vis Sci.* (Feb. 2000);41(2):568-579.

Patent Cooperation Treaty (PCT) International Search Report ; International Application No. PCT/US2005/013710, mailed on Dec. 23, 2005.

Rakoczy PE, Humphrey MF, Cavaney DM, Chu Y, Constable IJ. Expression of basic fibroblast growth factor and its receptor in the retina of Royal College of Surgeons rats. A comparative study. *Invest Ophthalmol Vis Sci.* (1993) vol. 34(5):1845-1852.

Rukenstein A, Rydel RE, and Greene LA, Multiple agents rescue PC12 cells from serum-free cell death by translation- and transcription-independent mechanisms, *J. Neurosci.* (1991) 11: 2552-2563.

Sivalingam A, Kenney J, Brown GC, Benson WE, Donoso L. Basic fibroblast growth factor levels in the vitreous of patients with proliferative diabetic retinopathy. *Arch Ophthalmol.* (1990) vol. 108(6):869-872.

(56) References Cited

OTHER PUBLICATIONS

L. Sobrin, T.A. Young, A. Sharma, T. Nakazawa, C.L. Grosskreutz, D.N. Zacks, J.W. Miller. Pigment epithelial-derived factor (PEDF) inhibits apoptosis in a rat model of retinal detachment. *The Aging Eye ARVO 2004 Annual Meeting*, Program#/Poster#: 2064/B875.
Tezel G, Yang X, Yang J, Wax MB. Role of tumor necrosis factor receptor-1 in the death of retinal ganglion cells following optic nerve crush injury in mice. *Brain Res.* (Jan. 23, 2004);996(2):202-212.
Wenzel A, Grimm C, Seeliger MW, Jaissle G, Hafezi F, Kretschmer R, Zrenner E, and Remé CE, Prevention of Photoreceptor Apoptosis by Activation of the Glucocorticoid Receptor, *Investigative Ophthalmology & Visual Science* (2001) vol. 42: 1653-1659.
Westra I, Robbins SG, Wilson DJ, Robertson JE, O'Rourke LM, Hart CE, Rosenbaum JT. Time course of growth factor staining in a rabbit model of traumatic tractional retinal detachment. *Graefes Arch Clin Exp Ophthalmol.* (Sep. 1995);233(9):573-581.
Zhang X, Chintala SK. Influence of interleukin-1 beta induction and mitogen-activated protein kinase phosphorylation on optic nerve ligation-induced matrix metalloproteinase-9 activation in the retina. *Exp Eye Res.* (2004) vol. 78(4):849-860.
Abcam, TNF Receptor II antibody [80M2] (ab17038), one page.
Ahmed et al. (2004), "Microarray analysis of changes in mRNA levels in the rat retina after experimental elevation of intraocular pressure," *Invest Ophthalmol Vis Sci*, 45: 1247-58.
Aihara et al. (2003), Experimental mouse ocular hypertension: establishment of the model, *Invest Ophthalmol Vis Sci*, 44:4314-20.
Alldred (2001) "Etanercept in rheumatoid arthritis," Expert Opin Pharmacother. 2: 1137-48.
Beckman et al. (1984), "Transcleral ruby laser coagulation," Am. J. Ophthalmol., 98:788-95.
Bietti (1950), "Surgical intervention on the ciliary body; new trends for the relief of glaucoma," JAMA, 142:889-97.
BMA Biomedicals, Monoclonal Antibody to Human CD120b Anti-human Tumor Necrosis Factor (TNF)—Receptor p75, 2 pages.
Bohatschek et al. (2004), "Microglial major histocompatibility complex glycoprotein-1 in the axotomized facial motor nucleus: regulation and role of tumor necrosis factor receptors 1 and 2," J Comp Neurol, 470:382-99.
Brouckaert et al. (1993) "Tumor necrosis factor, its receptors and the connection with interleukin 1 and interleukin 6," Immunobiology 187: 317-29.
Butt et al. (1994) "Morphological changes in oligodendrocytes in the intact mouse optic nerve following intravitreal injection of tumour necrosis factor," J Neuroimmunol. 51: 27-33.
Chen et al. (2002), "Distribution, markers, and functions of retinal microglia," Ocul Immunol Inflamm, 10:27-39.
Chung et al., "Ankyrin repeat and SOCS box 3 (ASB3) mediates ubiquitination and degradation of tumor necrosis factor receptor II," *Molecular and Cellular Biology* 200506 US, vol. 25, No. 11, Jun. 2005, pp. 4716-4726.
Coleman et al. (2005) "Axon degeneration mechanisms: commonality amid diversity," Nat Rev Neurosci. 6: 889-98.
Cordeiro et al. (2004), "Real-time imaging of single nerve cell apoptosis in retinal neurodegeneration," Proc Natl Acad Sci (USA), 101:13352-56.
De Keyser et al. (2006) "Anti-TNF-alpha therapy in ankylosing spondylitis," Cytokine 33(5): 294-98.
Diem et al. (2001), "Reduction of potassium currents and phosphatidylinositol 3-kinase-dependent AKT phosphorylation by tumor necrosis factor-(alpha) rescues axotomized retinal ganglion cells from retrograde cell death in vivo," *J Neurosci*, 21: 2058-66.
Dopp et al. (1997) "Differential expression, cytokine modulation, and specific functions of type-1 and type-2 tumor necrosis factor receptors in rat glia," J Neuroimmunol. 75: 104-112.
Dopp et al. (2002) "Expression of the p75 TNF receptor is linked to TNF-induced NFkappaB translocation and oxyradical neutralization in glial cells," Neurochem Res. 27: 1535-42.

Dziewulska et al. (2003) "Cellular expression of tumor necrosis factor a and its receptors in human ischemic stroke," Clin Neuropathol. 22: 35-40.
Follett et al. (2004), "Glutamate receptor-mediated oligodendrocyte toxicity in periventricular leukomalacia: a protective role for topiramate," J Neurosci, 24:4412-20.
Fontaine et al. (2002) "Neurodegenerative and Neuroprotective Effects of Tumor Necrosis Factor (TNF) in Retinal Ischemia: Opposite Roles of TNF Receptor 1 and TNF Receptor 2," J Neurosci. 22 RC216 (1-7).
Fuchs et al. (2005) "Retinal-cell-conditioned medium prevents TNF-alpha-induced apoptosis of purified ganglion cells," Invest Ophthalmol Vis Sci. 46(8): 2983-91.
Funayama et al. (2004) "Variants in optineurin gene and their association with tumor necrosis factor-alpha polymorphisms in Japanese patients with glaucoma," Invest Ophthalmol Vis Sci, 45: 4359-67.
Gould et al. (2004), "Anterior segment development relevant to glaucoma," Int J Dev Biol, 48:1015-29.
Guo et al. (2006) "Assessment of neuroprotective effects of glutamate modulation on glaucoma-related retinal ganglion cell apoptosis in vivo," Invest Ophthalmol Vis Sci, 47:626-33.
Haddad (1981), "Cyclocryotherapy. Experimental studies of the breakdown of the blood-aqueous barrier and analysis of a long term follow-up study (author's transl)," Wien. Klin. Wochenschr. Suppl. 126:3-18.
Haynes et al. (2005), "Oxidative and nitrative injury in periventricular leukomalacia: a review," Brain Pathol, 15:225-233.
Health Care Republic News, "Glaucoma damage reduced by rheumatoid arthritis drugs," Internet Citation, [Online] Dec. 8, 2006, p. 1.
Heijl et al. (2002), "Reduction of intraocular pressure and glaucoma progression: results from the Early Manifest Glaucoma Trial," Arch Ophthalmol, 120:1268-1279.
Horie, et al., "Interferon-gamma rescues TNF-alpha-induced apoptosis mediated by up-regulation of TNFR2 on EoL-1 cells," *Experimental Hematology* 199903 US, vol. 27, No. 3, Mar. 1999, pp. 512-519.
Hsiao et al. (2003) "Peptides identify multiple hotspots within the ligand binding domain of the TNF receptor 2," Proteome Sci. 1:1. Published online Jan. 24, 2003. doi: 10.1186/1477-5956-1-1.
Huang et al. (2005a), "Transcriptional up-regulation and activation of initiating caspases in experimental glaucoma," Am J Pathol, 167:673-81.
Huang et al. (2005b), "Calcineurin cleavage is triggered by elevated intraocular pressure, and calcineurin inhibition blocks retinal ganglion cell death in experimental glaucoma," Proc Natl Acad Sci (USA), 102:12242-47.
Iwase et al. (2004), "The prevalence of primary openangle glaucoma in Japanese: the Tajimi Study," Ophthalmology, 111:1641-8.
Ji et al. (2005) "Effects of elevated intraocular pressure on mouse retinal ganglion cells," Vision Res. 45:169-79.
John (2005), "Mechanistic insights into glaucoma provided by experimental genetics the cogan lecture," Invest Ophthalmol Vis Sci, 46:2650-61.
Kaiden et al. (1979), "Choroidal detachment with flat anterior chamber after cyclocryotherapy," Ann. Ophthalmol., 11:1111-3.
Kitaoka et al. (2006) "TNF-alpha-induced optic nerve degeneration and nuclear factor kappaB p. 65," Invest Ophthalmol Vis Sci. 47:1448-57.
Lane et al. (2005), "Lipid homeostasis and apolipoprotein E in the development and progression of Alzheimer's disease," J Lipid Res, 46:949-68.
Levin (2003), "Retinal ganglion cells and neuroprotection for glaucoma," Surv Ophthalmol, 48:S21-24.
Levkovitch-Verbin et al. (2006), "Minocyline Delays Death of Retinal Ganglion Cells in Experimental Glaucoma and After Optic Nerve Transection," Arch. Ophthalmol, 124:520-6.
Lindsey et al. (2005), "Elevated intraocular pressure and transgenic applications in the mouse," J Glaucoma, 14:318-20.

(56) References Cited

OTHER PUBLICATIONS

Lubing et al., (2005), "Endogenous TNF alpha mediates cell survival and chemotherapy resistance by activating the PI3K/Akt pathway in childhood acute lymphoblastic leukemia." Abstract, one page.
Mabuchi et al. (2004), "Optic nerve damage in mice with a targeted type I collagen mutation," Invest Ophthalmol Vis Sci, 45:1841-5.
MacEwan (2002), "TNF Liquids and Receptors in a matter of life and death," British Journal of Pharmacology, 135:855-75.
Matsubara et al. (2006), "Investigating the effect of ciliary body photodynamic therapy in a glaucoma mouse model," Invest Ophthalmol Vis Sci, 47:2498-2507.
Matute et al. (2001) "The link between excitotoxic oligodendroglial death and demyelinating diseases," Trends Neurosci. 24:224-30.
Miller et al. (2005) "A sublethal dose of TNFalpha potentiates kainate-induced excitotoxicity in optic nerve oligodendrocytes," Neurochem Res. 30:867-75.
Moss et al. (1997) "Structural features and biochemical properties of TNFalpha converting enzyme (TACE)," J Neuroimmunol. 72:127-9.
Moss et al. (2001) "TACE and other ADAM proteases as targets for drug discovery," Drug Discov Today 6:41 7-26.
Nakazawa et al. (2002a), "Brain-derived neurotrophic factor prevents axotomized retinal ganglion cell death through MAPK and PI3K signaling pathways," Invest Ophthalmol Vis Sci, 43:3319-26.
Nakazawa et al. (2002b), "Neuroprotective effect of nipradilol on axotomized rat retinal ganglion cells," Curr Eye Res, 24:114-22.
Nakazawa et al. (2005), "Selective up-regulation of RB3/stathmin4 by ciliary neurotrophic factor following optic nerve axotomy," Brain Res, 1061(2):97-106.
Nakazawa et al., "Tumor necrosis factor-[alpha] mediates oligodendrocyte death and delayed retinal ganglion cell loss in a mouse model of glaucoma," *Journal of Neuroscience* Dec. 6, 2006 US, vol. 26, No. 49, Dec. 6, 2006, pp. 12633-12641.
Patent Cooperation Treaty (PCT) International Search Report; International Application No. PCT/US2007/024256, mailed on Jun. 16, 2008.
Pease et al. (2000), "Obstructed axonal transport of BDNF and its receptor TrkB in experimental glaucoma," Invest Ophthalmol Vis Sci, 41:764-74.
Quigley (1996) "Number of people with glaucoma worldwide," Br J Ophthalmol. 80: 389-393.
R&D Systems, Inc., "Monoclonal Anti-human TNF RII/TNFRSF1B Antibody," Catalog No. MAB226, Nov. 25, 2002, 2 pages.
Raivich et al. (2003), "Lymphocyte infiltration in the injured brain: role of proinflammatory cytokines," J Neurosci Res, 72:726-33.
Resnikoff et al. (2004), "Global data on visual impairment in the year 2002," Bull World Health Organ, 82:844-51.
Santa Cruz Biotechnology, Inc., TNF-R2 (80M2): sc-52742, one page.
Saurenmann et al., "Tumour necrosis factor [alpha] inhibitors in the treatment of childhood uveitis," *Rheumatology* Aug. 2006 GB, vol. 45, No. 8, Aug. 2006 (Aug. 2006), pp. 982-989.
Shohami et al. (1999), "Dual role of tumor necrosis factor alpha in brain injury," Cytokine Growth Factor Rev 10:119-130.
Smith et al. (1969), "Ocular hazards of transscleral laser radiation. II. Intraocular injury produced by ruby and neodymium lasers," Am. J. Ophthalmol. 67:100-10.
Stys et al. (2005), "General mechanisms of axonal damage and its prevention," J Neurol Sci, 233:3-13.
Tartaglia et al. (1992) "Two TNF receptors," Immunol Today 13:151-3.
Tezel et al. (2000) "Increased production of tumor necrosis factor-alpha by glial cells exposed to simulated ischemia or elevated hydrostatic pressure induces apoptosis in cocultured retinal ganglion cells," J. Neurosci. 20(23):8693-700.
Tezel et al. (2001) "TNF-alpha and TNF-alpha receptor-1 in the retina of normal and glaucomatous eyes," Invest. Ophthalmol. Vis. Sci, 42(8):1787-94.
Tezel et al. (2003), "Immunohistochemical assessment of the glial mitogen-activated protein kinase activation in glaucoma," Invest Ophthalmol Vis Sci, 44:3025-33.
Tezel et al. (2004), "The immune system and glaucoma," Curr Opin Ophthalmol, 15:80-84.
Tikka et al. (2001) "Minocycline provides neuroprotection against N-methyl- D-aspartate neurotoxicity by inhibiting microglia," J Immunol. 166:7527-33.
Weekers et al. (1961), "Effects of photocoagulation of ciliary body upon ocular tension," Am. J. Ophthalmol., 52:156-63.
Weinreb et al. (2004), "Primary open-angle glaucoma," Lancet, 363:1711-20.
Yan et al. (2000) "Matrix Metalloproteinases and tumor necrosis factor alpha in glaucomatous optic nerve head," Arch. Ophthalmol. 118(5):666-73.
Yin et al. (2006), "Oncomodulin is a macrophage-derived signal for axon regeneration in retinal ganglion cells," Nat Neurosci, 9:843-52.
Yuan et al. (2000) "Tumor necrosis factor-alpha: a potentially neurodestructive cytokine produced by glia in the human glaucomatous optic nerve head," Glia 32:42-50.
Yuan et al. (2001) "Activated microglia in the human glaucomatous optic nerve head," J Neurosci Res 64: 523-32.
Zillig et al. (2005), Overexpression and properties of wild-type and Tyr437His mutated myocilin in the eyes of transgenic mice, Invest Ophthalmol Vis Sci, 46:223-34.

\* cited by examiner

Duration of detachment (Days)

Duration of detachment (Days)

Duration of detachment (Days)

Duration of detachment (Days)

SEQUENCE LISTING

<160> NUMBER OF SEQ ID NOS: 46

<210> SEQ ID NO 1
<211> LENGTH: 19
<212> TYPE: PRT
<213> ORGANISM: Artificial Sequence
<220> FEATURE:
<223> OTHER INFORMATION: Caspase 1 inhibitor
<220> FEATURE:
<221> NAME/KEY: MISC_FEATURE
<222> LOCATION: (1)..(1)
<223> OTHER INFORMATION: Xaa is AC-Ala
<220> FEATURE:
<221> NAME/KEY: MISC_FEATURE
<222> LOCATION: (1)..(1)
<223> OTHER INFORMATION: Xaa is Ac-Ala
<220> FEATURE:
<221> NAME/KEY: MISC_FEATURE
<222> LOCATION: (19)..(19)
<223> OTHER INFORMATION: Xaa is Asp-aldehyde

<400> SEQUENCE: 1

Xaa Ala Val Ala Leu Leu Pro Ala Val Leu Leu Ala Leu Leu Pro Tyr
1               5                   10                  15

Val Ala Xaa

<210> SEQ ID NO 2
<211> LENGTH: 20
<212> TYPE: PRT
<213> ORGANISM: Artificial Sequence
<220> FEATURE:
<223> OTHER INFORMATION: Caspase 3 inhibitor
<220> FEATURE:
<221> NAME/KEY: MISC_FEATURE
<222> LOCATION: (1)..(1)
<223> OTHER INFORMATION: Xaa is Ac-Ala
<220> FEATURE:
<221> NAME/KEY: MISC_FEATURE
<222> LOCATION: (20)..(20)
<223> OTHER INFORMATION: Xaa is Asp-aldehyde

<400> SEQUENCE: 2

Xaa Ala Val Ala Leu Leu Pro Ala Val Leu Leu Ala Leu Leu Ala Pro
1               5                   10                  15

Asp Glu Val Xaa
            20

<210> SEQ ID NO 3
<211> LENGTH: 20
<212> TYPE: PRT
<213> ORGANISM: Artificial Sequence
<220> FEATURE:
<223> OTHER INFORMATION: Caspase 4 inhibitor
<220> FEATURE:
<221> NAME/KEY: MISC_FEATURE
<222> LOCATION: (1)..(1)
<223> OTHER INFORMATION: Xaa is Ac-Ala
<220> FEATURE:
<221> NAME/KEY: MISC_FEATURE
<222> LOCATION: (20)..(20)
<223> OTHER INFORMATION: Xaa is Pro-aldehyde

<400> SEQUENCE: 3

Xaa Ala Val Ala Leu Leu Pro Ala Val Leu Leu Ala Leu Leu Ala Pro
1               5                   10                  15

Leu Glu Val Xaa
            20

<210> SEQ ID NO 4

```
<211> LENGTH: 20
<212> TYPE: PRT
<213> ORGANISM: Artificial Sequence
<220> FEATURE:
<223> OTHER INFORMATION: Caspase 6 inhibitor
<220> FEATURE:
<221> NAME/KEY: MISC_FEATURE
<222> LOCATION: (1)..(1)
<223> OTHER INFORMATION: Xaa is Ac-Ala
<220> FEATURE:
<221> NAME/KEY: MISC_FEATURE
<222> LOCATION: (20)..(20)
<223> OTHER INFORMATION: Xaa is Asp-aldehyde

<400> SEQUENCE: 4

Xaa Ala Val Ala Leu Leu Pro Ala Val Leu Leu Ala Leu Leu Ala Pro
1               5                   10                  15

Val Glu Ile Xaa
            20

<210> SEQ ID NO 5
<211> LENGTH: 20
<212> TYPE: PRT
<213> ORGANISM: Artificial Sequence
<220> FEATURE:
<223> OTHER INFORMATION: Caspase 8 inhibitor
<220> FEATURE:
<221> NAME/KEY: MISC_FEATURE
<222> LOCATION: (1)..(1)
<223> OTHER INFORMATION: Xaa is Ac-Ala
<220> FEATURE:
<221> NAME/KEY: MISC_FEATURE
<222> LOCATION: (20)..(20)
<223> OTHER INFORMATION: X is Asp-aldehyde

<400> SEQUENCE: 5

Xaa Ala Val Ala Leu Leu Pro Ala Val Leu Leu Ala Leu Leu Ala Pro
1               5                   10                  15

Ile Glu Thr Xaa
            20

<210> SEQ ID NO 6
<211> LENGTH: 20
<212> TYPE: PRT
<213> ORGANISM: Artificial Sequence
<220> FEATURE:
<223> OTHER INFORMATION: Caspase 9 inhibitor
<220> FEATURE:
<221> NAME/KEY: MISC_FEATURE
<222> LOCATION: (1)..(1)
<223> OTHER INFORMATION: X is Ac-Ala
<220> FEATURE:
<221> NAME/KEY: MISC_FEATURE
<222> LOCATION: (20)..(20)
<223> OTHER INFORMATION: X is Asp-aldehyde

<400> SEQUENCE: 6

Xaa Ala Val Ala Leu Leu Pro Ala Val Leu Leu Ala Leu Leu Ala Pro
1               5                   10                  15

Leu Glu His Xaa
            20

<210> SEQ ID NO 7
<211> LENGTH: 24
<212> TYPE: DNA
<213> ORGANISM: Artificial Sequence
<220> FEATURE:
<223> OTHER INFORMATION: Primer nucleotide

<400> SEQUENCE: 7
```
cagtgaaact gcgaatggct catt                                            24

<210> SEQ ID NO 8
<211> LENGTH: 25
<212> TYPE: DNA
<213> ORGANISM: Artificial Sequence
<220> FEATURE:
<223> OTHER INFORMATION: Primer nucleotide

<400> SEQUENCE: 8
agatctcgat tatgtacggc tgccc                                           25

<210> SEQ ID NO 9
<211> LENGTH: 22
<212> TYPE: DNA
<213> ORGANISM: Artificial Sequence
<220> FEATURE:
<223> OTHER INFORMATION: Primer Nucleotide

<400> SEQUENCE: 9
tcttcctgcg catccatcca ga                                              22

<210> SEQ ID NO 10
<211> LENGTH: 22
<212> TYPE: DNA
<213> ORGANISM: Artificial Sequence
<220> FEATURE:
<223> OTHER INFORMATION: Primer Nucleotide

<400> SEQUENCE: 10
gaggtcaacc atacaccgtg ac                                              22

<210> SEQ ID NO 11
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 11
cttggacaga gccagcggat ttgt                                            24

<210> SEQ ID NO 12
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 12
gtactttctt cgtttgcagg tgcc                                            24

<210> SEQ ID NO 13
<211> LENGTH: 25
<212> TYPE: DNA
<213> ORGANISM: Artificial Sequence
<220> FEATURE:
<223> OTHER INFORMATION: Primer Nucleotide

<400> SEQUENCE: 13
tctgccacga tcttacaggt gaaca                                           25

<210> SEQ ID NO 14
<211> LENGTH: 25
<212> TYPE: DNA

```
<213> ORGANISM: Artificial Sequence
<220> FEATURE:
<223> OTHER INFORMATION: Primer Nucleotide

<400> SEQUENCE: 14
ggagtaatag ttcaactagg tccgc                                              25

<210> SEQ ID NO 15
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 15
taccctggca agagagacga ggaa                                               24

<210> SEQ ID NO 16
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 16
gcatagtatt tggtacgtgc cacc                                               24

<210> SEQ ID NO 17
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 17
tgcccttcgc gctgaccagt gaca                                               24

<210> SEQ ID NO 18
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 18
ttgttcgccg ccgtgaagga gctt                                               24

<210> SEQ ID NO 19
<211> LENGTH: 23
<212> TYPE: DNA
<213> ORGANISM: Artificial Sequence
<220> FEATURE:
<223> OTHER INFORMATION: Primer Nucleotide

<400> SEQUENCE: 19
ttcagttcgt gtgtggacca agg                                                23

<210> SEQ ID NO 20
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 20
tctacatgac acgaggcgac ttcg                                               24
```

<210> SEQ ID NO 21
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 21
agatgagtgt gccaacaggt gcat                                             24

<210> SEQ ID NO 22
<211> LENGTH: 23
<212> TYPE: DNA
<213> ORGANISM: Artificial Sequence
<220> FEATURE:
<223> OTHER INFORMATION: Primer Nucleotide

<400> SEQUENCE: 22
cccaaaccgg tacttaaact gga                                              23

<210> SEQ ID NO 23
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 23
cactgttaag catgtgccgg agaa                                             24

<210> SEQ ID NO 24
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 24
tgtagccggt tgaagaacta gacc                                             24

<210> SEQ ID NO 25
<211> LENGTH: 25
<212> TYPE: DNA
<213> ORGANISM: Artificial Sequence
<220> FEATURE:
<223> OTHER INFORMATION: Primer Nucleotide

<400> SEQUENCE: 25
cttgaacatg acccgagcac attct                                            25

<210> SEQ ID NO 26
<211> LENGTH: 23
<212> TYPE: DNA
<213> ORGANISM: Artificial Sequence
<220> FEATURE:
<223> OTHER INFORMATION: Primer Nucleotide

<400> SEQUENCE: 26
tctagagcgc cttggagtag cta                                              23

<210> SEQ ID NO 27
<211> LENGTH: 24
<212> TYPE: DNA
<213> ORGANISM: Artificial Sequence
<220> FEATURE:

```
<223> OTHER INFORMATION: Primer Nucleotide

<400> SEQUENCE: 27
cccagaccct cacactcaga tcat                                              24

<210> SEQ ID NO 28
<211> LENGTH: 23
<212> TYPE: DNA
<213> ORGANISM: Artificial Sequence
<220> FEATURE:
<223> OTHER INFORMATION: Primer Nucleotide

<400> SEQUENCE: 28
aagagaagtt ccctgttccg acg                                               23

<210> SEQ ID NO 29
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 29
tcaggaaggc agtgtcactc attg                                              24

<210> SEQ ID NO 30
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 30
ctactactgc tggacgatca caca                                              24

<210> SEQ ID NO 31
<211> LENGTH: 23
<212> TYPE: DNA
<213> ORGANISM: Artificial Sequence
<220> FEATURE:
<223> OTHER INFORMATION: Primer Nucleotide

<400> SEQUENCE: 31
aatggctctc cttcgacgtg aca                                               23

<210> SEQ ID NO 32
<211> LENGTH: 25
<212> TYPE: DNA
<213> ORGANISM: Artificial Sequence
<220> FEATURE:
<223> OTHER INFORMATION: Primer Nucleotide

<400> SEQUENCE: 32
ggtttattct cggttctcga cctcc                                             25

<210> SEQ ID NO 33
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 33
gccgttctat ctggctagca agga                                              24
```

```
<210> SEQ ID NO 34
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 34
agcaacctca ctctactgac tccg                                           24

<210> SEQ ID NO 35
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 35
atgcaggtct ctgtcacgct tctg                                           24

<210> SEQ ID NO 36
<211> LENGTH: 25
<212> TYPE: DNA
<213> ORGANISM: Artificial Sequence
<220> FEATURE:
<223> OTHER INFORMATION: Primer Nucleotide

<400> SEQUENCE: 36
ttctcttagt ggtcgtcgtc cacag                                          25

<210> SEQ ID NO 37
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 37
tcttccagga gtaccccgat gaga                                           24

<210> SEQ ID NO 38
<211> LENGTH: 23
<212> TYPE: DNA
<213> ORGANISM: Artificial Sequence
<220> FEATURE:
<223> OTHER INFORMATION: Primer Nucleotide

<400> SEQUENCE: 38
tacgtctagt acgcctagtt tgg                                            23

<210> SEQ ID NO 39
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 39
gcccagatac aacagaatgc ggtt                                           24

<210> SEQ ID NO 40
<211> LENGTH: 24
<212> TYPE: DNA
<213> ORGANISM: Artificial Sequence
<220> FEATURE:
<223> OTHER INFORMATION: Primer Nucleotide
```

```
<400> SEQUENCE: 40
gcagaacttt aggttgacga cctc                                              24

<210> SEQ ID NO 41
<211> LENGTH: 25
<212> TYPE: DNA
<213> ORGANISM: Artificial Sequence
<220> FEATURE:
<223> OTHER INFORMATION: Primer Nucleotide

<400> SEQUENCE: 41
ctcggaaact gactgatgtg gaagc                                             25

<210> SEQ ID NO 42
<211> LENGTH: 25
<212> TYPE: DNA
<213> ORGANISM: Artificial Sequence
<220> FEATURE:
<223> OTHER INFORMATION: Primer Nucleotide

<400> SEQUENCE: 42
ttctttcacg acctgtacct cctgt                                             25

<210> SEQ ID NO 43
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 43
acccaactat gatgcgagcc aact                                              24

<210> SEQ ID NO 44
<211> LENGTH: 23
<212> TYPE: DNA
<213> ORGANISM: Artificial Sequence
<220> FEATURE:
<223> OTHER INFORMATION: Primer Nucleotide

<400> SEQUENCE: 44
tcacgtaggc ctgcggattt taa                                               23

<210> SEQ ID NO 45
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 45
gctgtttcca acttcggcta cgat                                              24

<210> SEQ ID NO 46
<211> LENGTH: 24
<212> TYPE: DNA
<213> ORGANISM: Artificial Sequence
<220> FEATURE:
<223> OTHER INFORMATION: Primer Nucleotide

<400> SEQUENCE: 46
tcagacagta agtggcccga gaga                                              24
```

METHODS AND COMPOSITIONS FOR PRESERVING THE VIABILITY OF PHOTORECEPTOR CELLS

CROSS-REFERENCE TO RELATED APPLICATION

The present application is the national stage of International (PCT) Patent Application Serial No. PCT/US2005/013710, filed Apr. 22, 2005, and published under PCT Article 21(2) in English, which claims priority to and the benefit of U.S. Ser. No. 60/564,717, filed on Apr. 23, 2004, the entirety of both of which are incorporated herein by reference.

FIELD OF THE INVENTION

The invention relates generally to methods and compositions for preserving the viability of photoreceptor cells following retinal detachment, and more particularly the invention relates to compositions including, for example, a neuroprotective agent, and their use in maintaining the viability of photoreceptor cells following retinal detachment.

BACKGROUND

The retina is a delicate neural tissue lining the back of the eye that converts light stimuli into electric signals for processing by the brain. Within the eye, the retina is disposed upon underlying retinal pigment epithelium and choroid, which provide the retina with a supply of blood and nutrients. A common and potentially blinding condition known as retinal detachment occurs when the retina becomes disassociated from its underlying retinal pigment epithelium and/or choroid with the accumulation of fluid in the intervening space. The loss of visual function appears to be more pronounced when the retinal detachments involve the central macula.

Unless treated, retinal detachments often result in irreversible visual dysfunction, which can range from partial to complete blindness. The visual dysfunction is believed to result from the death of photoreceptor cells, which can occur during the period when the retina is detached from its underlying blood and nutrient supply. Reattachment of the retina to the back surface of the eye typically is accomplished surgically, and despite the good anatomical results of these surgeries (i.e., reattachment of the retina) patients often are still left with permanent visual dysfunction.

There is still a need for new methods and compositions for maintaining the viability of photoreceptor cells following retinal detachment and for preserving vision when the retina ultimately becomes reattached.

SUMMARY

Monocyte chemoattractant protein-1 (MCP-1), tumor necrosis factor-alpha (TNF-alpha), interleukin-1 beta (IL-1 beta), and/or basic fibroblast growth factor (bFGF) mRNA and/or protein expression levels are increased in the retina following retinal detachment. Modulating the activity of these targets provides a neuroprotective effect in the retina. Thus, modulating MCP-1, TNF-alpha, IL-1 beta, and/or bFGF can maintain the viability of photoreceptor cells following retinal detachment and preserve vision when the retina is reattached.

In one aspect, the invention provides a method of preserving the viability of photoreceptor cells disposed within a retina of a mammalian eye following retinal detachment. The method includes administering to a mammal having an eye in which a region of the retina has been detached an amount of a neuroprotective agent selected from a substance capable of suppressing endogenous MCP-1, a MCP-1 antagonist, a substance capable of suppressing endogenous TNF-alpha, a TNF-alpha antagonist, a substance capable of suppressing endogenous IL-1 beta, an IL-1 beta antagonist, a substance capable of inducing endogenous bFGF, exogenous bFGF, a bFGF mimetic, and combinations thereof sufficient to preserve the viability of photoreceptor cells disposed within the region of the detached retina. Suppressing endogenous cytokines such as MCP-1, TNF-alpha or IL-1 beta includes, but is not limited to, suppressing or otherwise interfering with expression of the gene encoding the cytokine, suppressing or otherwise interfering with the transcription of the gene into mRNA, and/or suppressing or otherwise interfering with the translation of the mRNA from the cytokine gene into a functional protein.

This aspect can have any of the following features. The neuroprotective agent can be administered to the mammal prior to reattachment of the region of detached retina. The neuroprotective agent can be administered to the mammal after reattachment of the region of detached retina. The neuroprotective agent can be administered locally or systemically. A plurality of neuroprotective agents can be administered to the mammal. At least one neuroprotective agent can be administered by intraocular, intravitreal, or transcleral administration. The neuroprotective agent can reduce the number of photoreceptor cells in the region that die following retinal detachment. The retinal detachment occurs as a result of a retinal tear, retinoblastoma, melanoma, diabetic retinopathy, uveitis, choroidal neovascularization, retinal ischemia, pathologic myopia, or trauma.

In another aspect, the invention provides a method of preserving the viability of photoreceptor cells in a mammalian eye following retinal detachment. More particularly, the invention provides a method of preserving the viability of photoreceptor cells disposed within a region of a retina that has become detached from its underlying retinal pigment epithelium and/or choroid. The method comprises administering to a mammal in need of such treatment an amount of a neuroprotective agent sufficient to preserve the viability of photoreceptor cells, for example, rods and/or cones, disposed within the region of the detached retina. Administration of the neuroprotective agent minimizes the loss of visual function resulting from the retinal detachment.

The neuroprotective agent reduces the number of photoreceptor cells in the region of the retina that, without treatment, would die following retinal detachment. It is understood that photoreceptor cells in the retina may die via a variety of cell death pathways, for example, via apoptotic and necrotic cell death pathways. It has been found, however, that upon retinal detachment, the photoreceptor cells undergo apoptotic cell death in the detached portion of the retina. Furthermore, one or more caspases, for example, caspase 3, caspase 7 and caspase 9, participate in the cascade of events leading to apoptotic cell death. Accordingly, neuroprotective agents useful in the practice of the invention can include, for example, an apoptosis inhibitor, for example, a caspase inhibitor, for example, one or more of, a caspase 3 inhibitor, a caspase 7 inhibitor, and a caspase 9 inhibitor.

Because photoreceptors die as a result of retinal detachment, administration of neuroprotective agents minimize or reduce the loss of photoreceptor cell viability until such time the retina becomes reattached to the choroid and an adequate blood and nutrient supply is once again restored. The neuroprotective agent minimizes the level of photoreceptor cell death, and maintains photoreceptor cell viability prior to reattachment of the detached region of the retina. Under certain circumstances, however, it may be beneficial to administer the neuroprotective agent for a period of time after a retinal detachment has been detected and/or the retina surgically reattached. This period of time may vary and can include, for example, a period of a week, two weeks, three weeks, a month, three months, six months, nine months, a year, and two years, after surgical reattachment.

The neuroprotective agent, for example, can be administered, either alone or in combination with a pharmaceutically acceptable carrier or excipient, by one or more routes. For example, the neuroprotective agent may be administered systemically, for example, via oral or parenteral routes, for example, via intravascular, intramuscular or subcutaneous routes. Alternatively, the neuroprotective agent may be administered locally, for example, via intraocular, intravitreal, intraorbital, or transcleral routes. Furthermore, it is contemplated that a plurality of neuroprotective agents, for example, a substance capable of suppressing endogenous MCP-1, a MCP-1 antagonist, a substance capable of suppressing endogenous TNF-alpha, a TNF-alpha antagonist, a substance capable of suppressing endogenous IL-1 beta, an IL-1 beta antagonist, a substance capable of inducing endogenous bFGF, exogenous bFGF, a bFGF mimetic, one or more caspase inhibitors, and combinations thereof, may be administered to the mammal to maintain viability of the photoreceptor cells disposed within the detached portion of the retina.

It is contemplated that the practice of the invention will be helpful in maintaining the viability of photoreceptor cells in retinal detachments irrespective of how the retinal detachments were caused. For example, it is contemplated that the practice of the method of the invention will be helpful in minimizing visual dysfunction resulting from retinal detachments caused by one or more of the following: a retinal tear, retinoblastoma, melanoma, diabetic retinopathy, uveitis, choroidal neovascularization, retinal ischemia, pathologic myopia, and trauma.

The foregoing aspects and embodiments of the invention may be more fully understood by reference to the following figures, detailed description and claims.

BRIEF DESCRIPTION OF THE DRAWINGS

The objects and features of the invention may be more fully understood by reference to the drawings described below in which.

DETAILED DESCRIPTION

Figure 1:
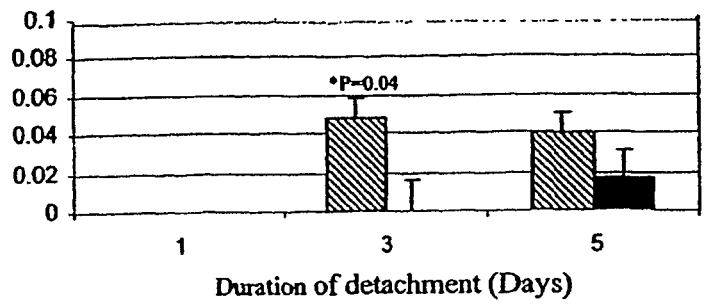
FIG. 1 depicts a bar chart showing the ratio of cleaved caspase 3 to pro-caspase 3 in densitometry units in detached retinas (hatched bars) and attached retinas (solid bars) at one, three and five days post retinal detachment.

During retinal detachment, the entire retina or a portion of the retina becomes dissociated from the underlying retinal pigment epithelium and choroid. As a result, the sensitive photoreceptor cells disposed in the detached portion of the retina become deprived of their normal supply of blood and nutrients. If untreated, the retina or more particularly the sensitive photoreceptor cells disposed within the retina die causing partial or even complete blindness. Accordingly, there is an ongoing need for methods and compositions that preserve the viability of photoreceptor cells following retinal detachment. If photoreceptor cell death can be minimized during retinal detachment, the affected photoreceptors likely will survive once the retina is reattached to the underlying retinal pigment epithelium and choroid, and the photoreceptors regain their normal blood and nutrient supply.

Retinal detachment can occur for a variety of reasons. The most common reason for retinal detachment involves retinal tears. Retinal detachments, however, can also occur because of, for example, retinoblastomas and other ocular tumors (for example, angiomas, melanomas, and lymphomas), diabetic retinopathy, retinal vascular diseases, uveitis, retinal ischemia and trauma. Furthermore, retinal detachments can occur as a result of formation of choroidal neovascularizations secondary to, for example, the neovascular form of age-related macular degeneration, pathologic myopia, and ocular histoplasmosis syndrome. It is understood that the clinical pathologies of retinal detachments are different from those of degenerative retinal disorders, for example, retinitis pigmentosa and age-related macular degeneration. However, the neuroprotective agents discussed herein may be useful in treating retinal detachments that occur secondary to an underlying degenerative retinal disorder. Accordingly, it is contemplated that the methods and compositions of the invention may be useful in minimizing or otherwise reducing photoreceptor cell death following retinal detachment, irrespective of the cause of the detachment.

The invention provides a method of preserving the viability of photoreceptor cells in a mammalian, for example, a primate, for example, a human, eye following retinal detachment. More particularly, the invention provides a method of preserving the viability of photoreceptor cells disposed within a region of a retina, which has become detached from its underlying retinal pigment epithelium and/or choroid. The method may be particularly helpful in preventing vision loss when the region of detachment includes at least a portion of the macula. The method comprises administering to a mammal in need of such treatment an amount of a neuroprotective agent sufficient to preserve the viability of photoreceptor cells disposed within the region of the detached retina.

As used herein, the term "neuroprotective agent" means any agent that, when administered to a mammal, either alone or in combination with other agents, minimizes or eliminates photoreceptor cell death (including both necrotic and apoptotic cell death) in a region of the retina that has become detached from the underlying retinal pigment epithelium and/or choroid. It is contemplated that useful neuroprotective agents include, for example, a substance capable of suppressing endogenous MCP-1, a MCP-1 antagonist, a substance capable of suppressing endogenous TNF-alpha, a TNF-alpha antagonist, a substance capable of suppressing endogenous IL-1 beta, an IL-1 beta antagonist, a substance capable of inducing endogenous bFGF, exogenous bFGF, a bFGF mimetic, combinations thereof, and apoptosis inhibitors, for example, caspase inhibitors, and certain neurotrophic factors that prevent the onset or progression of apoptosis. More specifically, useful neuroprotective agents may include, for example, a protein (for example, a growth factor, antibody or an antigen binding fragment thereof), a peptide (for example, an amino acid sequence less than about 25 amino acids in length, and optionally an amino acid sequence less that about 15 amino acids in length), a nucleic acid (for example, a deoxyribonucleic acid, ribonucleic acid, an antisense oligonucleotide, or an aptamer), a peptidyl nucleic acid (for example, an antisense peptidyl nucleic acid), an organic molecule or an inorganic molecule, which upon administration minimizes photoreceptor cell death following retinal detachment. Additionally, interfering RNA (RNAi) techniques can be used. Neuroprotective agents alternatively or additionally may protect against gliosis.

It is understood that photoreceptor cell death during retinal detachments may occur as a result of either necrotic or apoptotic (also known as programmed cell death) pathways. Both of these pathways are discussed in detail in, for example, Kerr et al. (1972) BR. J. CANCER 26: 239-257; Wyllie et al. (1980) INT. REV. CYTOLOGY 68: 251-306; Walker et al. (1988) METH. ACHIE. EXP. PATHOL. 13: 18-54 and Oppenheim (1991) ANN. REV. NEUROSCI. 14: 453-501. Apoptosis involves the orderly breakdown and packaging of cellular components and their subsequent removal by surrounding structures (Afford & Randhawa (2000) J. CLIN. PATHOL. 53:55-63). In general, apoptosis, also referred to as an apoptotic pathway, does not result in the activation of an inflammatory response. This is in contrast to necrotic cell death, which is characterized by the random breakdown of cells in the setting of an inflammatory response. Typically, during necrosis, also known as a necrotic pathway, a catastrophic event, for example, trauma, inflammation, ischemia or infection, typically causes uncontrolled death of a large group of cells. There are a variety of assays available for determining whether cell death is occurring via a necrotic pathway or an apoptotic pathway (see, for example, Cook et al. (1995) INVEST. OPHTHALMOL. VIS. SCI. 36:990-996).

Apoptosis involves the activation of a genetically determined cell suicide program that results in a morphologically distinct form of cell death characterized by cell shrinkage, nuclear condensation, DNA fragmentation, membrane reorganization and blebbing (Kerr et al. (1972) BR. J. CANCER 26: 239-257). Assays for detecting the presence of apoptotic pathways include measuring morphologic and biochemical stigmata associated with cellular breakdown and packaging, such as pyknotic nuclei, apoptotic bodies (vesicles containing degraded cell components) and internucleosomally cleaved DNA. This last feature is specifically detected by binding and labeling the exposed 3'-OH groups of the cleaved DNA with the enzyme terminal deoxynucleotidyl transferase in the staining procedure often referred to as the TdT-dUTP Terminal Nick End-Labeling (TUNEL) staining procedure. It is believed that, at the core of this process lies a conserved set of serine proteases, called caspases, which are activated specifically in apoptotic cells.

There are approximately fourteen known caspases, and the activation of these proteins results in the proteolytic digestion of the cell and its contents. Each of the members of the caspase family possess an active-site cysteine and cleave substrates at Asp-Xxx bonds (i.e., after the aspartic acid residue). In general, a caspase's substrate specificity typically is determined by the four residues amino-terminal to the cleavage site. Caspases have been subdivided into subfamilies based on their substrate specificity, extent of sequence identity and structural similarities, and include, for example, caspase 1, caspase 2, caspase 3, caspase 4, caspase 5, caspase 6, caspase 7, caspase 8, caspase 9, caspase 10, caspase 11, caspase 12, caspase 13 and caspase 14. Monitoring their activity can be used to assess the level of on-going apoptosis.

Furthermore, it has been suggested that apoptosis is associated with the generation of reactive oxygen species, and that the product of the $Bcl_{-2}$ gene protects cells against apoptosis by inhibiting the generation or the action of the reactive oxygen species (Hockenbery et al. (1993) CELL 75: 241-251, Kane et al. (1993) SCIENCE 262: 1274-1277, Veis et al (1993) CELL 75: 229-240, Virgili et al. (1998) FREE RADICALS BIOL. MED. 24: 93-101). $Bcl_{-2}$ belongs to a growing family of apoptosis regulatory gene products, which may either be death antagonists ($Bcl_{-2}$, $Bcl-x_L$) or death agonists (Bax, Bak) (Kroemer et al. (1997) NAT. MED. 3: 614-620). Control of cell death appears to be regulated by these interactions and by constitutive activities of the various family members (Hockenbery et al. (1993) CELL 75: 241-251). Several apoptotic pathways may coexist in mammalian cells that are preferentially activated in a stimulus-, stage-, context-specific and cell-type manner (Hakem et al. (1998) CELL 94: 339-352). However, it is contemplated that agents that upregulate the level of the Bcl-2 gene expression or slow down the rate of breakdown of the $Bcl_{-2}$ gene product may be useful in the practice of the invention.

Useful apoptosis inhibitors include, for example, (i) proteins, for example, growth factors, cytokines, antibodies and antigen binding fragments thereof (for example, Fab, Fab', and Fv fragments), genetically engineered biosynthetic antibody binding sites, also known in the art as BABS or sFv's, and (ii) peptides, for example, synthetic peptides and derivatives thereof, which may be administered systemically or locally to the mammal. Other useful apoptosis inhibitors include, for example, deoxyribonucleic acids (for example, antisense oligonucleotides), ribonucleic acids (for example, antisense oligonucleotides and aptamers) and peptidyl nucleic acids, which once administered reduce or eliminate expression of certain genes, for example, caspase genes as in the case of anti-sense molecules, or can bind to and reduce or eliminate the activity of a target protein or receptor as in the case of aptamers. Additionally, RNAi techniques can be used. Other useful apoptosis inhibitors include small organic or inorganic molecules that reduce or eliminate apoptotic activity when administered to the mammal.

One set of apoptosis inhibitors useful in the practice of the invention include caspase inhibitors. Caspase inhibitors include molecules that inhibit or otherwise reduce the catalytic activity of a target caspase molecule (for example, a classical competitive or non-competitive inhibitor of catalytic activity) as well as molecules that prevent the onset or initiation of a caspase mediated apoptotic pathway.

With regard to the inhibitors of catalytic function, it is contemplated that useful caspase inhibitors include, on the one hand, broad spectrum inhibitors that reduce or eliminate the activity of a plurality of caspases or, on the other hand, specific caspase inhibitors that reduce or eliminate the activity of a single caspase. In general, caspase inhibitors act by binding the active site of a particular caspase enzyme and forming either a reversible or an irreversible linkage to target caspase molecule. Caspase inhibitors may include inhibitors of one or more of caspase 1, caspase 2, caspase 3, caspase 4, caspase 6, caspase 7, caspase 8, caspase 9, caspase 10, caspase 11, caspase 12, caspase 13, and caspase 14.

Useful caspase inhibitors include commercially available synthetic caspase inhibitors. Synthetic caspase inhibitors typically include a peptide recognition sequence attached to a functional group such as an aldehyde, chloromethylketone, fluoromethylketone, or fluoroacyloxymethylketone. Typically, synthetic caspase inhibitors with an aldehyde functional group reversibly bind to their target caspases, whereas the caspase inhibitors with the other functional groups tend to bind irreversibly to their targets. Useful caspase inhibitors, when modeled with Michaelis-Menten kinetics, preferably have a dissociation constant of the enzyme-inhibitor complex ($K_i$) lower than 100 μM, preferably lower than 50 μM, more preferably lower than 1 μM. The peptide recognition sequence corresponding to that found in endogenous substrates determines the specificity of a particular caspase. For example, peptides with the Ac-Tyr-Val-Ala-Asp-aldehyde sequence are potent inhibitors of caspases 1 and 4 ($K_i$=10 nM), and are weak inhibitors of caspases 3 and 7 ($K_i \geq 50$ μM). Removal of the tyrosine residue, however, results in a potent but less specific inhibitor. For example, 2-Val-Ala-Asp-fluoromethylketone inhibits caspases 1 and 4 as well as caspases 3 and 7.

Exemplary synthetic caspase 1 inhibitors, include, for example, Ac-N-Me-Tyr-Val-Ala-Asp-aldehyde, Ac-Trp-Glu-His-Asp-aldehyde, Ac-Tyr-N-Me-Val-Ala-N-Me-Asp-aldehyde, Ac-Tyr-Val-Ala-Asp-Aldehyde, Ac-Tyr-Val-Ala-Asp-chloromethylketone, Ac-Tyr-Val-Ala-Asp-2,6-dimethylbenzoyloxymethylketone, Ac-Tyr-Val-Ala-Asp (OtBu)-aldehyde-dimethyl acetol, Ac-Tyr-Val-Lys-Asp-aldehyde, Ac-Tyr-Val-Lys(biotinyl)-Asp-2,6-dimethylbenzoyloxymethylketone, biotinyl-Tyr-Val-Ala-Asp-chloromethylketone, Boc-Asp(OBzl)-chloromethylketone, ethoxycarbonyl-Ala-Tyr-Val-Ala-Asp-aldehyde (pseudo acid), Z-Asp-2,6-dichlorobenzoyloxymethylketone, Z-Asp(OlBu)-bromomethylketone, Z-Tyr-Val-Ala-Asp-chloromethylketone, Z-Tyr-Val-Ala-DL-Asp-fluoromethlyketone, Z-Val-Ala-DL-Asp-fluoromethylketone, and Z-Val-Ala-DL-Asp(OMe)-fluoromethylketone, all of which can be obtained from Bachem Bioscience Inc., PA. Other exemplary caspase 1 inhibitors include, for example, Z-Val-Ala-Asp-fluoromethylketone, biotin-X-Val-Ala-Asp-fluoromethylketone, Ac-Val-Ala-Asp-aldehyde, Boc-Asp-fluoromethylketone, Ac-Ala-Ala-Val-Ala-Leu-Leu-Pro-Ala-Val-Leu-Leu-Ala-Leu-Leu-Pro-Tyr-Val-Ala-Asp-aldehyde (SEQ ID NO: 1), biotin-Tyr-Val-Ala-Asp-fluoroacyloxymethylketone, Ac-Tyr-Val-Ala-Asp-acyloxymethylketone, Z-Asp-CH2-DCB, Z-Tyr-Val-Ala-Asp-fluoromethylketone, all of which can be obtained from Calbiochem, CA.

Exemplary synthetic caspase 2 inhibitors, include, for example, Ac-Val-Asp-Val-Ala-Asp-aldehyde, which can be obtained from Bachem Bioscience Inc., PA, and Z-Val-Asp-Val-Ala-Asp-fluoromethylketone, which can be obtained from Calbiochem, CA.

Exemplary synthetic caspase 3 precursor protease inhibitors include, for example, Ac-Glu-Ser-Met-Asp-aldehyde (pseudo acid) and Ac-Ile-Glu-Thr-Asp-aldehyde (pseudo acid) which can be obtained from Bachem Bioscience Inc., PA. Exemplary synthetic caspase 3 inhibitors include, for example, Ac-Asp-Glu-Val-Asp-aldehyde, Ac-Asp-Met-Gin-Asp-aldehyde, biotinyl-Asp-Glu-Val-Asp-aldehyde, Z-Asp-Glu-Val-Asp-chloromethylketone, Z-Asp(OMe)-Glu (OMe)-Val-DL-Asp(OMe)-fluoromethylketone, and Z-Val-Ala-DL-Asp(OMe)-fluoromethylketone which can be obtained from Bachem Bioscience Inc., PA. Other exemplary caspase 3 inhibitors include, for example, Ac-Ala-Ala- Val-Ala-Leu-Leu-Pro-Ala-Val-Leu-Leu-Ala-Leu-Leu-Ala-Pro-Asp-Glu-Val-Asp-aldehyde (SEQ ID NO: 2), Z-Asp-Glu-Val-Asp-fluoromethylketone, biotin-X-Asp-Glu-Val-Asp-fluoromethylketone, Ac-Asp-Glu-Val-Asp-chloromethylketone, which can be obtained from Calbiochem, CA.

Exemplary synthetic caspase 4 inhibitors include, for example, Ac-Leu-Glu-Val-Asp-aldehyde and Z-Tyr-Val-Ala-DL-Asp-fluoromethylketone, which can be obtained from Bachem Bioscience Inc., PA, and Ac-Ala-Ala-Val-Ala-Leu-Leu-Pro-Ala-Val-Leu-Leu-Ala-Leu-Leu-Ala-Pro-Leu-Glu-Val-Pro-aldehyde (SEQ ID NO: 3), which can be obtained from Calbiochem, CA.

Exemplary synthetic caspase 5 inhibitors include, for example, Z-Trp-His-Glu-Asp-fluoromethylketone, which can be obtained from Calbiochem, CA, and Ac-Trp-Glu-His-Asp-aldehyde and Z-Trp-Glu(O-Me)-His-Asp(O-Me) fluoromethylketone, which can be obtained from Sigma Aldrich, Germany.

Exemplary synthetic caspase 6 inhibitors include, for example, Ac-Val-Glu-Ile-Asp-aldehyde, Z-Val-Glu-Ile-Asp-fluoromethylketone, and Ac-Ala-Ala-Val-Ala-Leu-Leu-Pro-Ala-Val-Leu-Leu-Ala-Leu-Leu-Ala-Pro-Val-Glu-Ile-Asp-aldehyde (SEQ ID NO: 4), which can be obtained from Calbiochem, CA.

Exemplary synthetic caspase 7 inhibitors include, for example, Z-Asp(OMe)-Gln-Met-Asp(OMe) fluoromethylketone, Ac-Asp-Glu-Val-Asp-aldehyde, Biotin-Asp-Glu-Val-Asp-fluoromethylketone, Z-Asp-Glu-Val-Asp-fluoromethylketone, Ac-Ala-Ala-Val-Ala-Leu-Leu-Pro-Ala-Val-Leu-Leu-Ala-Leu-Leu-Ala-Pro-Asp-Glu-Val-Asp-aldehyde (SEQ ID NO: 2), which can be obtained from Sigma Aldrich, Germany.

Exemplary synthetic caspase 8 inhibitors include, for example, Ac-Asp-Glu-Val-Asp-aldehyde, Ac-Ile-Glu-Pro-Asp-aldehyde, Ac-Ile-Glu-Thr-Asp-aldehyde, Ac-Trp-Glu-His-Asp-aldehyde and Boc-Ala-Glu-Val-Asp-aldehyde which can be obtained from Bachem Bioscience Inc., PA. Other exemplary caspase 8 inhibitors include, for example, Ac-Ala-Ala-Val-Ala-Leu-Leu-Pro-Ala-Val-Leu-Leu-Ala-Leu-Leu-Ala-Pro-Ile-Glu-Thr-Asp-aldehyde (SEQ ID NO: 5) and Z-Ile-Glu-Thr-Asp-fluoromethylketone, which can be obtained from Calbiochem, CA.

Exemplary synthetic caspase 9 inhibitors, include, for example, Ac-Asp-Glu-Val-Asp-aldehyde, Ac-Leu-Glu-His-Asp-aldehyde, and Ac-Leu-Glu-His-Asp-chloromethylketone which can be obtained from Bachem Bioscience Inc., PA. Other exemplary caspase 9 inhibitors include, for example, Z-Leu-Glu-His-Asp-fluoromethylketone and Ac-Ala-Ala-Val-Ala-Leu-Leu-Pro-Ala-Val-Leu-Leu-Ala-Leu-Leu-Ala-Pro-Leu-Glu-His-Asp-aldehyde (SEQ ID NO: 6), which can be obtained from Calbiochem, CA.

Furthermore, it is contemplated that caspase specific antibodies (for example, monoclonal or polyclonal antibodies, or antigen binding fragments thereof), for example, an antibody that specifically binds to and reduces the activity of, or inactivates a particular caspase may be useful in the practice of the invention. For example, an anti-caspase 3 antibody, an anti-caspase 7 antibody, or an anti-caspase 9 antibody may be useful in the practice of the invention. Additionally, it is contemplated that an anti-caspase aptamer that specifically binds and reduces the activity of, or inactivates a particular caspase, for example, an anti-caspase 3 aptamer, an anti-caspase 7 aptamer, or an anti-caspase 9 aptamer may be useful in the practice of the invention.

Alternatively, endogenous caspase inhibitors can be used to reduce, or inhibit caspase activity. For example, one useful class of endogenous caspase inhibitor includes proteins known as inhibitors of apoptosis proteins (IAPs) (Deveraux et al. (1998) EMBO JOURNAL 17(8): 2215-2223) including bioactive fragments and analogs thereof. One exemplary IAP includes X-linked inhibitor of apoptosis protein (XIAP), which has been shown to be a direct and selective inhibitor of caspase-3, caspase-7 and caspase-9. Another exemplary IAP includes survivin (see, U.S. Pat. No. 6,245,523; Papapetropoulos et al. (2000) J. BIOL. CHEM. 275: 9102-9105), including bioactive fragments and analogs thereof. Survivin has been reported to inhibit caspase-3 and caspase-7 activity. It is also contemplated that molecules that act through IAPs will also be useful, for example, VEGF has anti-apoptotic activity by acting through survivin.

In addition, it is contemplated that useful neuroprotective agents may include one or more neurotrophic factors, which may serve as effective apoptosis inhibitors (Lewis et al. (1999) INVEST. OPHTHALMOL. VIS. SCI. 40: 1530-44; LaVail et al. (1998) INVEST. OPHTHALMOL. VIS. SCI. 39: 592-602). Exemplary neurotrophic factors include, for example, Brain Derived Growth Factor (Caffe et al. (2001) INVEST OPHTHALMOL. VIS. SCI. 42: 275-82) including bioactive fragments and analogs thereof; Fibroblast Growth Factor (Bryckaert et al. (1999) ONCOGENE 18: 7584-7593) including bioactive fragments and analogs thereof; PEDF including bioactive fragments and analogs thereof; and Insulin-like Growth Factors, for example, IGF-I and IGF-II (Rukenstein et al. (1991) J NEUROSCI. 11:2552-2563) including bioactive fragments and analogs thereof; and cytokine-associated neurotrophic factors.

Bioactive fragments refer to portions of an intact template protein that have at least 30%, more preferably at least 70%, and most preferably at least 90% of the biological activity of the intact proteins. Analogs refer to species and allelic variants of the intact protein, or amino acid replacements, insertions or deletions thereof that have at least 30%, more preferably at least 70%, and most preferably 90% of the biological activity of the intact protein.

With reference to the foregoing proteins, the term "analogs" includes variant sequences that are at least 80% similar or 70% identical, more preferably at least 90% similar or 80% identical, and most preferably 95% similar or 90% identical to at least a portion of one of the exemplary proteins described herein, for example, Brain Derived Growth Factor. To determine whether a candidate protein has the requisite percentage similarity or identity to a reference polypeptide, the candidate amino acid sequence and the reference amino acid sequence are first aligned using the dynamic programming algorithm described in Smith and Waterman (1981) J. MOL BIOL. 147:195-197, in combination with the BLOSUM62 substitution matrix described in FIG. 2 of Henikoff and Henikoff (1992), PROC. NAT. ACAD. SCI. USA 89:10915-10919. An appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art. Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pairwise similarity score is zero; otherwise the pairwise similarity score is 1.0. The raw similarity score is the sum of the pairwise similarity scores of the aligned amino acids. The raw score is then normalized by dividing it by the number of amino acids in the smaller of the candidate or reference sequences. The normalized raw score is the percent similarity.

Alternatively, to calculate a percent identity, the aligned amino acids of each sequence are again compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

Furthermore, by way of example, cAMP elevating agents may also serve as effective apoptosis inhibitors. Exemplary cAMP elevating agents include, for example, 8-(4-chloro-phenylthio)-adenosine-3':5'-cyclic-monophosphate (CPT-cAMP) (Koike (1992) PROG. NEURO-PSYCHOPHARMACOL. BIOL. PSYCHIAT. 16: 95-106), forskolin, isobutyl methylxanthine, cholera toxin (Martin et al. (1992) J. NEUROBIOL. 23:1205-1220), and 8-bromo-cAMP, $N^6$, $O^{2'}$-dibutyryl-cAMP and $N^6, O^{2'}$ dioctanoyl-cAMP (Rydel and Greene (1988) PROC. NAT. ACAD. SCI. USA 85: 1257-1261).

Furthermore, other exemplary apoptosis inhibitors can include, for example, glutamate inhibitors, for example, NMDA receptor inhibitors (Bamford et al. (2000) EXP. CELL RES. 256: 1-11) such as eliprodil (Kapin et al. (1999) INVEST. OPHTHALMOL. VIS. SCI 40, 1177-82) and MK-801 (Solberg et al. INVEST. OPHTHALMOL. VIS. SCI (1997) 38, 1380-1389) and n-acetylated-αλπηα-linked-acidic dipeptidase inhibitors, such as, 2-(phosphonomethyl) pentanedioic acid (2-PMPA) (Harada et al. NEUR. LETT. (2000) 292, 134-36); steroids, for example, hydrocortisone and dexamethasone (see, U.S. Pat. No. 5,840,719; Wenzel et al. (2001) INVEST. OPHTHALMOL. VIS. SCI. 42: 1653-9); nitric oxide synthase inhibitors (Donovan et al. (2001) J. BIOL. CHEM. 276: 23000-8); serine protease inhibitors, for example, 3,4-dichloroisocoumarin and N-tosyl-lysine chloromethyl ketone (see, U.S. Pat. No. 6,180,402); cysteine protease inhibitors, for example, N-ethylmaleimide and iodoacetamide, or an interleukin-1β-converting enzyme inhibitor, for example, Z-Asp-2,6-dichlorobenzoyloxymethylketone (see, U.S. Pat. No. 6,180,402); and antisense nucleic acid or peptidyl nucleic acid sequences that lower of prevent the expression of one or more of the death agonists, for example, the products of the Bax, and Bak genes.

In addition, or in the alternative, it may be useful to inhibit expression or activity of members of the caspase cascade that are upstream or downstream of caspase 3, caspase 7 and caspase 9. For example, it may be useful to inhibit PARP, which is a component of the apoptosis cascade downstream of caspase 7. An exemplary PARP inhibitor includes 3-aminobenzamide (Weise et al. (2001) CELL DEATH DIFFER. 8:801-807). Other examples include inhibitors of the expression or activity of Apoptosis Activating Factor-1 (Apaf-1) and/or cytochrome C. Apaf-1 and cytochrome C bind the activated form of caspase 9 to produce a complex, which is known to propagate the apoptosis cascade. Thus, any protein (for example, antibody), nucleic acid (for example, aptamer), peptidyl nucleic acid (for example, antisense molecule) or other molecule that inhibits or interferes with the binding of caspase 9 to Apaf-1/cytochrome C can serve to inhibit apoptosis.

Under certain circumstances, it may be advantageous to also administer to the individual undergoing treatment with the neuroprotective agent an anti-permeability agent and/or an inflammatory agent so as to minimize photoreceptor cell death. An anti-permeability agent is a molecule that reduces the permeability of normal blood vessels. Examples of such molecules include molecules that prevent or reduce the expression of genes encoding, for example, Vascular Endothelial Growth Factor (VEGF) or an Intercellular Adhesion Molecule (ICAM) (for example, ICAM-1, ICAM-2 or ICAM-3). Exemplary molecules include antisense oligonucleotides and antisense peptidyl nucleic acids that hybridize in vivo to a nucleic acid encoding a VEGF gene, an ICAM gene, or a regulatory element associated therewith. Other suitable molecules bind to and/or reduce the activity of, for example, the VEGF and ICAM molecules (for example, anti-VEGF and anti-ICAM antibodies and antigen binding fragments thereof, and anti-VEGF or anti-ICAM aptamers). Other suitable molecules bind to and prevent ligand binding and/or activation of a cognate receptor, for example, the VEGF receptor or the ICAM receptor. Such molecules may be administered to the individual in an amount sufficient to reduce the permeability of blood vessels in the eye. An anti-inflammatory agent is a molecule that prevents or reduces an inflammatory response in the eye and in some instances can be considered a neuroprotective agent. Exemplary anti-inflammatory agents include steroids, for example, hydrocortisone, dexamethasone sodium phosphate, and methylpredisolone. Such molecules may be administered to the individual in an amount sufficient to reduce or eliminate an inflammatory response in the eye.

It is contemplated that the foregoing and other neuroprotective agents now known or hereafter discovered may be assayed for efficacy in minimizing photoreceptor cell death following retinal detachment using a variety of model systems. Basic techniques for inducing retinal detachment in various animal models are known in the art (see, for example, Anderson et al. (1983) INVEST. OPHTHALMOL. VIS. SCI. 24: 906-926; Cook et al. (1995) INVEST. OPHTHALMOL. VIS. SCI. 36: 990-996; Marc et al. (1998) OPHTHALMOL. VIS. SCI. 39: 1694-1702; Mervin et al. (1999) AM. J. OPHTHALMOL. 128: 155-164; Lewis et al. (1999) AM. J. OPHTHALMOL. 128: 165-172). Once a suitable animal model has been created (see, Example 1 below) an established or putative neuroprotective agent can be administered to an eye at different dosages. The ability of the neuroprotective agent and dosage required to maintain cell viability may be assayed by one or more of (i) tissue histology, (ii) TUNEL staining, which quantifies the number of TUNEL-positive cells per section, (iii) electron microscopy, (iv) immunoelectron microscopy to detect the level of, for example, apoptosis inducing factor (AIF) in the samples, and (v) immunochemical analyses, for example, via Western blotting, to detect the level of certain caspases in a sample.

The TUNEL technique is particularly useful in observing the level of apoptosis in photoreceptor cells. By observing the number of TUNEL-positive cells in a sample, it is possible to determine whether a particular neuroprotective agent is effective at minimizing or reducing the level of apoptosis, or eliminating apoptosis in a sample. For example, the potency of the neuroprotective agent will have an inverse relationship to the number of TUNEL-positive cells per sample. By comparing the efficacy of a variety of potential neuroprotective agents using these methods, it is possible to identify neuroprotective factors most useful in the practice of the invention.

The neuroprotective agent may be administered to the mammal from the time the retinal detachment is detected to the time the retina is repaired, for example, via surgical reattachment. It is understood, however, that under certain circumstances, it may be advantageous to administer the neuroprotective agent to the mammal even after the retina has been surgically repaired. For example, even after the surgical reattachment of a detached retina in patients with rhegmatogenous retinal detachments, persistent subretinal fluid may exist under the fovea as detected by ocular coherence tomography long after the surgery has been performed (see, Hagimura et al. (2002) AM. J. OPHTHALMOL. 133:516-520). As a result, even after surgical repair the retina may still not be completely reattached to the underlying retinal pigment epithelium and choroid. Furthermore, when retinal detachments occur secondary to another disorder, for example, the neovascular form of age-related macular degeneration and ocular melanomas, it may be beneficial to administer the neuroprotective agent to the individual while the underlying disorder is being treated so as to minimize loss of photoreceptor cell viability. Accordingly, in such cases, it may be advantageous to administer the neuroprotective agent to the mammal for one week, two weeks, three weeks, one month, three months, six months, nine months, one year, two years or more (i) after retinal detachment has been identified, and/or (ii) after surgical reattachment of the retina has occurred, and/or (iii) after detection of an underlying degenerative disorder, so as to minimize photoreceptor cell death.

Once the appropriate neuroprotective agents have been identified, they may be administered to the mammal of interest in any one of a wide variety of ways. It is contemplated that a neuroprotective agent, for example, a caspase inhibitor, can be administered either alone or in combination with another neuroprotective agent, for example, a neurotrophic agent. It is contemplated that the efficacy of the treatment may be enhanced by administering two, three, four or more different neuroprotective agents either together or one after the other. Although the best means of administering a particular neuroprotective agent or combination of neuroprotective agents may be determined empirically, it is contemplated that neuroprotective agents may be administered locally or systemically.

Systemic modes of administration include both oral and parenteral routes. Parenteral routes include, for example, intravenous, intrarterial, intramuscular, intradermal, subcutaneous, intranasal and intraperitoneal routes. It is contemplated that the neuroprotective agents administered systemically may be modified or formulated to target the neuroprotective agent to the eye. Local modes of administration include, for example, intraocular, intraorbital, subconjuctival, intravitreal, subretinal or transcleral routes. It is noted, however, that local routes of administration are preferred over systemic routes because significantly smaller amounts of the neuroprotective agent can exert an effect when administered locally (for example, intravitreally) versus when administered systemically (for example, intravenously). Furthermore, the local modes of administration can reduce or eliminate the incidence of potentially toxic side effects that may occur when therapeutically effective amounts of neuroprotective agent (i.e., an amount of a neuroprotective agent sufficient to reduce, minimize or eliminate the death of photoreceptor cells following retinal detachment) are administered systemically.

Administration may be provided as a periodic bolus (for example, intravenously or intravitreally) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag). The neuroprotective agent may be administered locally, for example, by continuous release from a sustained release drug delivery device immobilized to an inner wall of the eye or via targeted transscleral controlled release into the choroid (see, for example, PCT/US00/00207, PCT/US02/14279, Ambati et al. (2000) INVEST. OPHTHALMOL. VIS. SCI. 41:1181-1185, and Ambati et al. (2000) INVEST. OPHTHALMOL. VIS. SCI. 41:1186-1191). A variety of devices suitable for administering a neuroprotective agent locally to the inside of the eye are known in the art. See, for example, U.S. Pat. Nos. 6,251,090, 6,299,895, 6,416,777, 6,413,540, and 6,375,972, and PCT/US00/28187.

The neuroprotective agent also may be administered in a pharmaceutically acceptable carrier or vehicle so that administration does not otherwise adversely affect the recipient's electrolyte and/or volume balance. The carrier may comprise, for example, physiologic saline or other buffer system.

In addition, it is contemplated that the neuroprotective agent may be formulated so as to permit release of the neuroprotective agent over a prolonged period of time. A release system can include a matrix of a biodegradable material or a material which releases the incorporated neuroprotective agent by diffusion. The neuroprotective agent can be homogeneously or heterogeneously distributed within the release system. A variety of release systems may be useful in the practice of the invention, however, the choice of the appropriate system will depend upon rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that neuroprotective agents having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

One of the primary vehicles currently being developed for the delivery of ocular pharmacological agents is the poly (lactide-co-glycolide) microsphere for intraocular injection. The microspheres are composed of a polymer of lactic acid and glycolic acid, which are structured to form hollow spheres. These spheres can be approximately 15-30 μm in diameter and can be loaded with a variety of compounds varying in size from simple molecules to high molecular weight proteins such as antibodies. The biocompatibility of these microspheres is well established (see, Sintzel et al. (1996) EUR. J. PHARM. BIOPHARM. 42: 358-372), and microspheres have been used to deliver a wide variety of pharmacological agents in numerous biological systems. After injection, poly(lactide-co-glycolide) microspheres are hydrolyzed by the surrounding tissues, which cause the release of the contents of the microspheres (Zhu et al. (2000) NAT. BIOTECH. 18: 52-57). As will be appreciated, the in vivo half-life of a microsphere can be adjusted depending on the specific needs of the system.

The type and amount of neuroprotective agent administered may depend upon various factors including, for example, the age, weight, gender, and health of the individual to be treated, as well as the type and/or severity of the retinal detachment to be treated. As with the modes of administration, it is contemplated, that the optimal neuroprotective agents and dosages of those neuroprotective agents may be determined empirically. The neuroprotective agent preferably is administered in an amount and for a time sufficient to permit the survival of at least 25%, more preferably at least 50%, and most preferably at least 75%, of the photoreceptor cells in the detached region of the retina.

By way of example, protein-, peptide- or nucleic acid-based neuroprotective agents can be administered at doses ranging, for example, from about 0.001 to about 500 mg/kg, optionally from about 0.01 to about 250 mg/kg, and optionally from about 0.1 to about 100 mg/kg. Nucleic acid-based neuroprotective agents may be administered at doses ranging from about 1 to about 20 mg/kg daily. Furthermore, antibodies that are neuroprotective agents may be administered intravenously at doses ranging from about 0.1 to about 5 mg/kg once every two to four weeks. With regard to intravitreal administration, the neuroprotective agents, for example, antibodies, may be administered periodically as boluses in dosages ranging from about 10 μg to about 5 mg/eye, and optionally from about 100 μg to about 2 mg/eye. With regard to transcleral administration, the neuroprotective agents may be administered periodically as boluses in dosages ranging from about 0.1 μg to about 1 mg/eye, and optionally from about 0.5 μg to about 0.5 mg/eye.

The present invention, therefore, includes the use of a neuroprotective agent, for example, a substance capable of suppressing endogenous MCP-1, a MCP-1 antagonist, a substance capable of suppressing endogenous TNF-alpha, a TNF-alpha antagonist, a substance capable of suppressing endogenous IL-1 beta, an IL-1 beta antagonist, a substance capable of inducing endogenous bFGF, exogenous bFGF, a bFGF mimetic, a caspase inhibitor, and combinations thereof, in the preparation of a medicament for treating an ocular condition associated with a retinal detachment, for example, a loss of vision as a result of photoreceptor cell death in the region of retinal detachment. A composition comprising one or more neuroprotective agents, one agent optionally being a caspase inhibitor, may be provided for use in the present invention. The neuroprotective agent or agents may be provided in a kit which optionally may comprise a package insert with instructions for how to treat the patient with the retinal detachment. For each administration, the neuroprotective agent may be provided in unit-dosage or multiple-dosage form. Preferred dosages of the neuroprotective agents, however, are as described above.

It has also been observed, as more fully described in Examples 3 and 4 below, that mRNA levels of bFGF, TNF-alpha, and IL-1 beta, and protein levels of bFGF, TNF-alpha, and IL-1 beta increase in retinas in response to detachment of the retina from the underlying choroidal tissue. bFGF is a cytokine that has anti-inflammatory activity, while TNF-alpha and IL-1 beta are cytokines with pro-inflammatory activity. Accordingly, to the extent the viability of photoreceptor cells disposed within a retina (as well as other cells disposed within the retina) is to be preserved, steps may be taken to exploit these natural biological responses by either enhancing the anti-inflammatory substance or suppressing the pro-inflammatory substance.

For example, insofar as bFGF has anti-inflammatory activity, it is possible to enhance the level of bFGF by either further inducing its production or exogenously adding it, in order to provide further anti-inflammatory activity. Similarly, it is possible to add exogenous molecules that mimic the activity of bFGF (a bFGF mimetic). Any of these routes may preserve the viability of photoreceptor cells disposed within a retina. Examples of the neuroprotective agents that can enhance the level of bFGF, supplement the level of bFGF, or mimic the activity of bFGF, include proteins or peptides that are inducers of the bFGF gene, exogenous bFGF itself (whether isolated from a natural source or manufactured using recombinant DNA techniques), peptides from the active portion of the full size bFGF protein, and small molecules. In some instances, one or more of the following may be useful to modulate bFGF: growth hormone (increases bFGF-mRNA), TGF-beta 1 (upregulates bFGF-mRNA expression and bFGF levels), cell-associated heparin-like molecules and heparan sulfate proteoglycans (controls bioavailability of bFGF to ocular cells), prostaglandin E2 (stimulates bFGF-mRNA expression), prolactin (stimulates bFGF-mRNA expression), nicotine (regulates bFGF production and increases bFGF-mRNA), CS23 (acid-stable mutein of bFGF which up-regulates bFGF-mRNA expression), forskolin and PMA (increases bFGF-mRNA expression), acidosis (enhances bFGF-mRNA expression as well as bFGF secretion), NYAG (Naoyi'an granule, may enhance bFGF expression and suppress TNF), huangpi when paired with TGF-beta 1 (may increase bFGF), lansoprazole (increases bFGF levels), Silicone-containing gel dressing (Silastic (SGS) and ClearSite) (increases levels of bFGF), angiotensin II (increases bFGF expression), Luteinizing hormone (increases bFGF expression), and finasteride (decreases bFGF levels—to the extent bFGF decrease is desired). It should be understood that any of the dosage strategies, drug formulations, or administration schedules described above are applicable to all of these neuroprotective agents.

Conversely, insofar as TNF-alpha and IL-1 beta have pro-inflammatory activity, one may decrease the level of one or both of these cytokines or otherwise antagonize one or both of their activities, in order to reduce the pro-inflammatory activity. Examples of the neuroprotective agents that can suppress the level of TNF-alpha or antagonize the activity of TNF-alpha, include, for example, etanercept (Example 5, below), estrogen (decreases TNF gene expression), inhibition of p38 MAPK (decreases TNF-alpha expression), chronic garlic administration (decreases TNF-alpha expression), eicosapentaenoic acid (decreases TNFalpha expression), and TBP2 and TBP3 (decrease TNF-alpha activity). Neuroprotective agents can also include growth factors, cytokines, antibodies, for example TNF-alpha blocking antibody as described in Example 6, below, and Di62—anti-TNF-alpha monoclonal antibody (decreases TNF-alpha activity), and antigen binding fragments thereof (for example, Fab, Fab', and Fv fragments), genetically engineered biosynthetic antibody binding sites, also known in the art as BABS or sFv's, and peptides, for example, synthetic peptides and derivatives thereof, which may be administered to systemically or locally to the mammal. Other useful neuroprotective agents include, for example, deoxyribonucleic acids (for example, antisense oligonucleotides), ribonucleic acids (for example, antisense oligonucleotides, aptamers, and interfering RNA) and peptidyl nucleic acids, which once administered reduce or eliminate expression of certain genes or can bind to and reduce or eliminate the activity of a target protein or receptor as in the case of aptamers. Other useful neuroprotective agents include small organic or inorganic molecules that reduce or eliminate activity when administered to the mammal. Any of these routes may preserve the viability of photoreceptor cells disposed within a retina. It should be understood that any of the dosage strategies, drug formulations, or administration schedules described above are applicable to all of these neuroprotective agents.

Examples of the neuroprotective agents that can suppress the level of IL-1 beta or antagonize the activity of IL-1 beta, include pseudo-ICE and ICEBERG (block IL-1 beta secretion), polymorphonuclear cell (PMN) inhibitors (decrease IL-1), glucocorticoids (decrease IL-1 beta expression), cyclosporine combined with a steroid (decreases IL-1 expression), 15-deoxy-Delta(12,14)-PGJ2 (PGJ2, decreases IL-1 beta and TNF-alpha expression and increases IL-1rn expression), PPARgamma ligands (decrease IL-1 secretion), cPKC and nPKC (decrease IL-1 beta and TNF-alpha production), IL-1rn (IL-1 antagonist), PMA (increases IL-1rn expression), IL-10 (increases IL-1rn), retinoic acid (upregulates IL-1 beta—to the extent an increase in IL-1 is desired), phorbol esters (increase IL-1 beta expression,—to the extent an increase in IL-1 is desired), IFNs (increase or decrease IL-1/IL-1rn), and lipopolysaccharide (increases IL-1rn expression and increases IL-1). Neuroprotective agents also include growth factors, cytokines, antibodies and antigen binding fragments thereof (for example, Fab, Fab', and Fv fragments), genetically engineered biosynthetic antibody binding sites, also known in the art as BABS or sFv's, and (ii) peptides, for example, synthetic peptides and derivatives thereof, which may be administered to systemically or locally to the mammal. Other useful neuroprotective agents include, for example, deoxyribonucleic acids (for example, antisense oligonucleotides), ribonucleic acids (for example, antisense oligonucleotides, aptamers, and interfering RNA) and peptidyl nucleic acids, which once administered reduce or eliminate expression of certain genes or can bind to and reduce or eliminate the activity of a target protein or receptor as in the case of aptamers. Other useful neuroprotective agents include small organic or inorganic molecules that reduce or eliminate activity when administered to the mammal. Any of these routes may preserve the viability of photoreceptor cells disposed within a retina. It should be understood that any of the dosage strategies, drug formulations, or administration schedules described above are applicable to all of these neuroprotective agents.

One or more of these cytokines can be modulated to preserve the viability of photoreceptor cells disposed within a retina (as well as other cells disposed within the retina). It should be understood that any of the dosage strategies, drug formulations, or administration schedules described above are applicable to all of these neuroprotective agents. Additionally, while treatments involving these cytokine responses in detached retinas above are described with relation to their anti- or pro-inflammatory activity and potential for inducing cell death, to the extent another mechanism is involved (for example, the ability of these cytokines to affect a undesirable proliferative change in photoreceptor cells or apoptosis), similar strategies can be used to choose neuroprotective agents that modulate the cytokines.

In addition, as shown in Examples 3 and 4, MCP-1 mRNA and MCP-1 protein are increased in detached retinas as compared to non-detached retinas. The increase in this factor can induce migration of microglia and macrophages to the detachment area for phagocytosis of the debris produced by apoptotic photoreceptors. These monocytes also may be related to secretion of TNF-alpha, and further destruction of photoreceptors. Immunohistochemistry data indicates that MCP-1 (and bFGF) was increased in Muller cells three days after retinal detachment, and microglia migrate toward the Muller cells, which increase the MCP-1 protein. Insofar as microglia and macrophages may be secondarily toxic to photoreceptors, suppression of the increase of MCP-1 following retinal detachment may be beneficial.

Examples of the neuroprotective agents that can suppress the level of MCP-1 or antagonize the activity of MCP-1, include, for example, ADR7 and ADR22 (MCP-1 antagonists), renin-angiotensin system (RAS) inhibitors (decreases MCP-1 expression), naked plasmid encoding 7ND (MCP-1 antagonist), dilazep (inhibits MCP-1 mRNA expression), fenofibric acid (inhibits MCP-1 mRNA expression), cetirizine (decreases MCP-1 levels), tenidap (decreases MCP-1 expression), dexamethasone (decreases MCP-1 mRNA expression), IFN-gamma (inhibits lipopolysaccharide-inducible MCP-1), blockers of PTK and PKC which are needed for MCP-1 gene expression in human monocytes, triple helix-forming oligonucleotides (TFO's) (selective inhibitor of MCP-1 gene expression), LY294002 (inhibits MCP-1 expression), olmesartan (inhibits MCP-1 and TNF expression), suppressors of NF-kappaB (inhibits MCP-1 expression), wogonin (inhibits MCP-1 expression), and Platelet-activating factor (PAF) (stimulates MCP-1 expression—to the extent an increase in IL-1 is desired). Neuroprotective agents can also include growth factors, cytokines, antibodies and antigen binding fragments thereof (for example, Fab, Fab', and Fv fragments), genetically engineered biosynthetic antibody binding sites, also known in the art as BABS or sFv's, and (ii) peptides, for example, synthetic peptides and derivatives thereof, which may be administered to systemically or locally to the mammal. Other useful neuroprotective agents include, for example, deoxyribonucleic acids (for example, antisense oligonucleotides), ribonucleic acids (for example, antisense oligonucleotides, aptamers, and interfering RNA) and peptidyl nucleic acids, which once administered reduce or eliminate expression of certain genes or can bind to and reduce or eliminate the activity of a target protein or receptor as in the case of aptamers. Other useful neuroprotective agents include small organic or inorganic molecules that reduce or eliminate activity when administered to the mammal. Any of these routes may preserve the viability of photoreceptor cells disposed within a retina. These neuroprotective agents can be used in combination with the neuroprotective agents described above, for example with the neuroprotective agents related to the cytokines described above. It should be understood that any of the dosage strategies, drug formulations, or administration schedules described above are applicable to all of these neuroprotective agents.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

In light of the foregoing description, the specific non-limiting examples presented below are for illustrative purposes and not intended to limit the scope of the invention in any way.

EXAMPLES

Example 1

Detection of Caspase Activity Following Retinal Detachment

This example demonstrates that certain caspases, particularly caspases 3, 7 and 9, are activated in photoreceptor cells following retinal detachment.

Experimental retinal detachments were created using modifications of previously published protocols (Cook et al. (1995) INVEST. OPHTHALMOL. VIS. SCI. 36(6):990-6; Hisatomi et al. (2001) AM. J. PATH. 158(4):1271-8). Briefly, rats were anesthetized using a 50:50 mixture of ketamine (100 mg/ml) and xylazine (20 mg/ml). Pupils were dilated using a topically applied mixture of phenylephrine (5.0%) and tropicamide (0.8%). A 20 gauge micro-vitreoretinal blade was used to create a sclerotomy approximately 2 mm posterior to the limbus. Care was taken not to damage the lens during the sclerotomy procedure. A Glaser subretinal injector (20 gauge shaft with a 32 gauge tip, Beckton-Dickinson, Franklin Lakes, N.J.) connected to a syringe filled with 10 mg/ml of Healon® sodium hyaluronate (Pharmacia and Upjohn Company, Kalamazoo, Mich.) then was introduced into the vitreous cavity. The tip of the subretinal injector was used to create a retinotomy in the peripheral retina, and then the sodium hyaluronate was slowly injected into the subretinal space to elevate the retina from the underlying retinal pigment epithelium. Retinal detachments were created only in the left eye (OS) of each animal, with the right eye (OD) serving as the control. In each experimental eye, approximately one half of the retina was detached, allowing the attached portion to serve as a further control.

Following creation of the experimental retinal detachment, intraocular pressures were measured before and immediately after retinal detachment with a Tono-pen. No differences in intraocular pressures were noted. The retinal break created by the subretinal injector was confined only to the site of the injection.

Light microscopic analysis of the detached retinas showed an increase in morphologic stigmata of apoptosis as a function of time after detachment. Eyes then were enucleated one, three, five and seven days after creation of the retinal detachment. For light microscopic analysis, the cornea and lens were removed and the remaining eyecup placed in a fixative containing 2.5% glutaraldehyde and 2% formaldehyde in 0.1M cacodylate buffer (pH 7.4) and stored at 4° C. overnight. Tissue samples then were post-fixed in 2% osmium tetroxide, dehydrated in graded ethanol, and embedded in epoxy resin. One-micron sections were stained with 0.5% toluidine blue in 0.1% borate buffer and examined with a Zeiss photomicroscope (Axiophot, Oberkochen, Germany).

At one day after creation of the detachment, pyknosis in the ONL was confined to the area of the peripheral retinotomy site through which the subretinal injector was introduced. By three days, however, pyknotic nuclei were seen in the whole ONL of the retina in the area of the detachment. Extrusion of pyknotic nuclei from the ONL into the subretinal space was observed. The remaining layers of the retina appeared morphologically normal. No inflammatory cells were seen, and there was no apparent disruption of the retinal vasculature. Similar changes were seen in sections from retinas detached for up to one week. No pyknotic nuclei were seen in the area of the attached retina or in the fellow, non-detached eye. The amount of ONL pyknosis was similar between detachments of three-day or one week duration.

Disruption of the photoreceptor outer segments was a prominent feature in the detached retinas. Outer segments of the control eyes and the attached portions of the experimental eyes had an orderly, parallel arrangement. Detachments produced artifactually during tissue processing in these eyes did not alter the photoreceptor morphology. In contrast, the photoreceptor outer segments of detached retinas were severely disorganized and lost their normal structural organization. Additionally, outer segments in attached areas had similar lengths, whereas the outer segments in detached areas showed variable lengths.

Internucleosomal DNA cleavage in photoreceptor cells was detected via TUNEL staining. For TUNEL staining, the cornea and lens were not removed after enucleation, but rather the whole eye was fixated overnight at 4° C. in a phosphate buffered saline solution of 4% paraformaldehyde solution (pH 7.4). Then, a section was removed from the superior aspect of the globe and the remaining eyecup embedded in paraffin and sectioned at a thickness of 6 μm. TUNEL staining was performed on these sections using the TdT-Fragel DNA Fragmentation Detection Kit (Oncogene Sciences, Boston, Mass.) in accordance with the manufacturer's instructions. Reaction signals were amplified using a preformed avidin: biotinylated-enzyme complex (ABC-kit, Vector Laboratories, Burlingame, Calif.). Internucleosomally cleaved DNA fragments were stained with diaminobenzidine (DAB) (staining indicates TUNEL-positive cells) and sections were then counterstained with methylene green.

TUNEL-positive cells were detected at all time points tested (one, three, five and seven days post-detachment). TUNEL-positive staining was confined only to the photoreceptor cell layer. Two eyes with retinal detachments that persisted for two months were monitored. The TUNEL assay at two months did not reveal any staining indicating the presence of internucleosomally cleaved DNA. The prolonged detachment was associated with a marked reduction in the thickness of and number of cell bodies contained in the ONL as compared to the non-detached retina.

Antibodies specific for caspases 3, 7, 9 and PARP were used in Western blots to probe total retinal protein extracts at various times after creation of the retinal detachment. For Western blot analysis, retinas from both experimental and control eyes were manually separated from the underlying retinal pigment epithelium/choroid at days one, three and five after creation of the retinal detachment. In eyes with retinal detachments, the experimentally detached portion of the retina was separated from the attached portion of the retina and analyzed separately. Retinas were homogenized and lysed with buffer containing 1 mM ethylene diaminetetraacetic acid/ethylene glycol-bis (2-aminoethylethel-N,N, N',N'-tetraacetic acid/dithiothreitol, 10 mM HEPES pH 7.6, 0.5% (octylphenoxy)polyethoxyethanol (IGEPAL), 42 mM potassium chloride, 5 mM magnesium chloride, 1 mM phenylmethanesulfonyl fluoride and 1 tablet of protease inhibitors per 10 ml buffer (Complete Mini, Roche Diagnostics GmbH, Mannheim, Germany). Samples were incubated for 15 minutes on ice, and then centrifuged at 21,000 rpm at 4° C. for 30 minutes. The protein concentration of the supernatant was determined using the Bio-Rad $D_C$ Protein Assay reagents (Bio-Rad Laboratories, Hercules, Calif.).

Proteins were separated via sodium dodecyl sulfate-polyacrylamide gel electrophoresis (7.5% and 15% Tris-HCL Ready-Gels, Bio-Rad Laboratories), in which 30 μg of total retinal protein were applied in each lane. The fractionated proteins were transferred to a PVDF membrane (Immobilon-P, Millipore, Bedford, Mass.). The resulting membrane was blocked with 5% non-fat dry milk in 0.1% TBST IGEPAL. The blocked membranes then were incubated with antibodies against caspase 7 (1:1,000; Cell Signaling Technology, Beverly, Mass.), caspase 9 (1:1,000; Medical & Biological Laboratories, Naka-ku Nagoya, Japan), cleaved-caspase 3 (1:1,000; Cell Signaling Technology, Beverly, Mass.), caspase 3 (1:2000; Santa Cruz, Santa Cruz, Calif.) or PARP (1:1000; Cell Signaling Technologies, Beverly, Mass.) overnight at 4° C. Bands were detected using the ECL-Plus reagent (Amersham, Pharmacia, Piscataway, N.J.). Membranes were exposed to HyperFilm (Amersham) and densitometry was preformed using ImageQuant 1.2 software (Molecular Dynamics, Inc., Sunnyvale, Calif.). For each eye tested, densitometry levels were normalized by calculating the ratio of the cleaved-form to the pro-form of the protein of interest. Pro-caspase 7 levels were normalized to the densitometry readings from a non-specific band detected by the secondary IgG. Five eyes were used for each time point, except for the PARP levels for day 5 after detachment for which only four eyes were used. All statistical comparisons were performed using a paired t-test.

The cleaved, or active form of caspase 3 was elevated in the detached retinas as compared to the attached retinas. The level of cleaved-caspase 3 increased as a function of time after detachment, with a peak at approximately three days (see, FIG. 1). No cleaved-caspase 3 was detected in the control eye or in the attached portion of the retina in the experimental eye.

Figure 2:
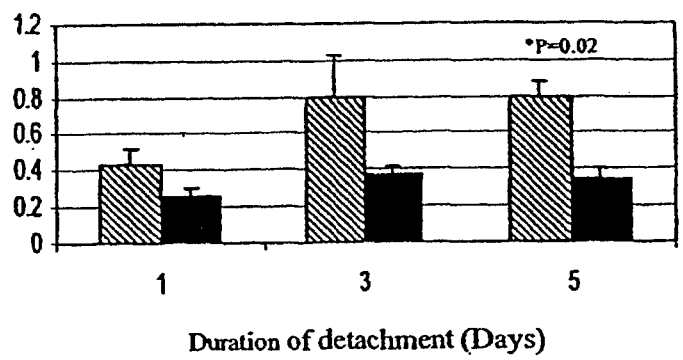
FIG. 2 depicts a bar chart showing the ratio of cleaved caspase 9 to pro-caspase 9 in densitometry units in detached retinas (hatched bars) and attached retinas (solid bars) at one, three and five days post retinal detachment.
Figure 3:
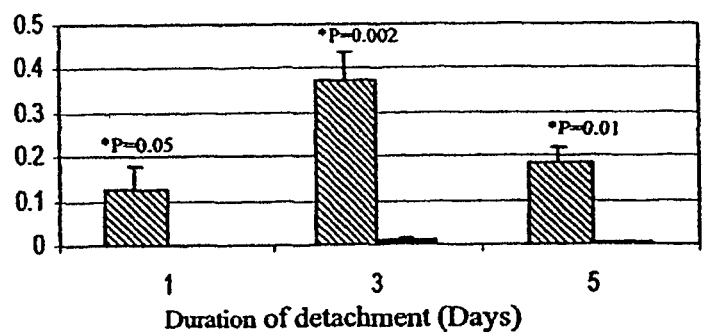
FIG. 3 depicts a bar chart showing the level of caspase 7 in densitometry units in detached retinas (hatched bars) and attached retinas (solid bars) at one, three and five days post retinal detachment.
Figure 4:
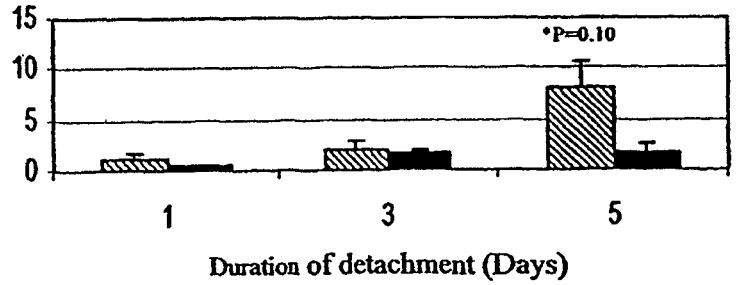
FIG. 4 depicts a bar chart showing the ratio of cleaved poly-ADP ribose-polymerase (PARP) to pro-PARP in densitometry units in detached retinas (hatched bars) and attached retinas (solid bars) at one, three and five days post retinal detachment.

The ratio of the active to inactive form of caspase 9 also increased as a function of time after creation of the experimental retinal detachment (see, FIG. 2). The peak level of cleaved-caspase 9 was seen at three to five days after creation of the detachment. The caspase 7 antibody was able only to detect the pro-form of the protein. There was, however, a significant difference in the amount of the pro-form detected in the protein extract from the detached retinas as compared to the attached retinas (see, FIG. 3). Western blotting with antibodies against PARP (a component of the apoptosis cascade downstream of caspase 7) detected an increase in the level of cleaved-PARP that was maximal at five days after detachment (see, FIG. 4). P-values for the comparisons between detached and attached retinas are shown in FIGS. 1-4.

The results demonstrate that caspase 3, caspase 7 and caspase 9 are all activated in photoreceptor cells following retinal attachment.

Example 2

Preservation of Photoreceptor Viability Following Retinal Detachment

The type of experiment provided herein may show that the viability of photoreceptor cells in a detached region of a retina can be maintained by administering a caspase inhibitor to an affected eye.

Retinal detachments are surgically induced in Brown-Norway rats as discussed in Example 1. The caspase inhibitor, Z-Val-Ala-Asp-fluoromethylketone is dissolved in dimethyl sulfoxide (DMSO) to give the final concentrations of 0.2 mM, 2 mM, and 20 mM. After creating the retinotomy with the subretinal injector, a small amount of Healon® sodium hyaluronate is injected in the subretinal space so as to elevate the retina. After retinal elevation, a Hamilton syringe with a 33 gauge needle is introduced through the retinotomy site, and 25 μl of inhibitor is injected into the region of detachment. About 25 minutes later, Healon® sodium hyaluronate is injected, via the same retinotomy site, to maintain the retinal detachment. Healon® sodium hyaluronate is injected until resistance is detected.

Only the right eyes of rats are used in evaluating the role of the Z-VAD-FMK inhibitor. The left eyes serve as the controls. Five animals are used for each concentration of inhibitor (namely, no inhibitor, 0.2 mM inhibitor, 2 mM inhibitor, and 20 mM inhibitor). For the no inhibitor control, 25 μl of DMSO is injected into the region of detachment followed by Healon® sodium hyaluronate.

After 72 hours, the eyes are enucleated and the rats euthanized. The enucleated eyes are paraffin embedded as described in Example 1. Then, 6 μm sections from the posterior segments are analyzed by TUNEL staining as described in Example 1. It is contemplated that there will be fewer photoreceptor cells in the region of retinal detachment that stain TUNEL-positive in eyes treated with the caspase inhibitor relative to eyes that have not been treated with the caspase inhibitor.

Example 3

Detection of mRNA Levels of bFGF, TNF-alpha, IL-1 Beta, and MCP-1

This example demonstrates that mRNA levels of bFGF, TNF-alpha, IL-1 beta, and MCP-1 increase in retinal samples following retinal detachment.

Two groups of eyes from six adult male Brown Norway rats (300-450 g, Charles River, Boston, Mass.) were examined. One group of eyes was the control group having non-detached retinas, while the other group of eyes was the experimental group having detached retinas (each rat had one control and one experimental eye). Rats were anesthetized with a 50:50 mixture of ketamine (100 mg/mL) and xylazine (20 mg/mL) (both from Phoenix Pharmaceutical, St. Joseph, Mo.). Pupils were dilated with a topically applied mixture of phenylephrine (5.0%) and tropicamide (0.8%). A sclerotomy was created approximately 2 mm posterior to the limbus with a 20-gauge needle. Care was taken not to damage the lens during creation of the sclerotomy. A Glaser subretinal injector (20-gauge shaft with a 32-gauge tip, BD Biosciences, Franklin Lakes, N.J.) connected to a syringe filled with 10 mg/mL Healon® sodium hyaluronate (Pharmacia and Upjohn Co., Kalamazoo, Mich.) was then introduced into the vitreous cavity. A retinotomy was created in the peripheral retina with the tip of the subretinal injector, and the sodium hyaluronate was slowly injected into the subretinal space. Thus, one half of the retina was detached. Retinal detachments were created only in the right eye of each animal, with the left eye serving as the control. Three days after retinal detachment, the rats were sacrificed with an overdose of sodium pentobarbital and the eyes were enucleated. The neural retina was dissected in a cold pool of PBS and frozen immediately with powdered dry ice.

Total RNA was extracted with a Micro-to-Midi™ Total RNA Purification System (Invitrogen, Carlsbad, Calif.) according to the manufacture's instructions. Each retina was homogenized manually with 600 µl of RNA lysis solution, and the same volume of 70% ethanol was added. The mixture was applied to an RNA spin cartridge and centrifuged at 12,000×g for 15 seconds at 25° C. The cartridge was washed with wash buffer I and twice with wash buffer II. Total RNA was eluted with 30 µl of RNase-free water. To decrease the contamination of genomic DNA, DNase I (Invitrogen) was added followed by a 15 minute incubation at room temperature. The concentration of total RNA was measured with a UV spectrometer (MUTO, JAPAN). Three micrograms of total RNA was used in a reverse transcription reaction using the SuperScript III First-Strand Synthesis System for RT-PCR (Invitrogen). First-strand cDNA was amplified using an ABI7700 real-time PCR system with a SYBR® green PCR core kit (Applied Biosystems) and PCR primer sets as listed in Table 1, in which the forward primers (F1) appear in the 5' to 3' direction from left to right and the reverse primers (R1) appear in the 3' to 5' direction from left to right.

PCR amplification was performed for 40 cycles with two step PCR methods. Denaturation was at 96° C. for 30 seconds and annealing and extension were at 60° C. for 90 seconds. The quality of PCR products was evaluated by agarose gel electrophoresis and staining with ethidium bromide. For relative comparison of each gene, the Ct value of real-time PCR data was analyzed with the 2(-Delta Delta C(T)) method (Livak et al. (2001) METHODS. 25: 402-8). To standardize the amount of sample cDNA added to each reaction, the Ct value of each target gene was subtracted by the Ct value of endogenous control (18 rRNA).

The data from the experimental and control groups were analyzed using a T-test and StatView 4.11J software for the Macintosh computer (Abacus concepts Inc., Berkeley, Calif.). The significance level was set at P<0.05 (*). All values are expressed as the mean±standard deviation (SD). The bar chart shown in FIG. 6 indicates the expressional change of each mRNA examined by real-time PCR of the six rats 3 days following retinal detachment. The Y axis presents the relative value of the experimental right eye versus the untreated left control eye. bFGF, TNF-alpha, IL-1 beta, and MCP-1 were significantly increased 3 days after retinal detachment.

Figure 5:
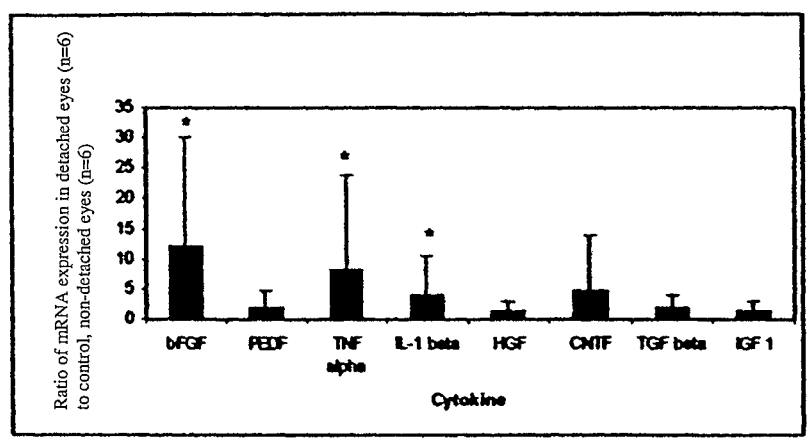
FIG. 5 depicts a bar chart showing the retinal mRNA expression of various types of mRNA in detached retina versus non-detached retina.

Additionally, for each type of mRNA of interest (bFGF, PEDF, TNF-alpha, IL-1 beta, HGF, CNTF, TGF beta, and IGF 1), the amount of mRNA from each of the six eyes of a group was averaged. Then, the average amount of a type of mRNA from the detached group was compared with the amount of a type of mRNA from the non-detached group. The results are shown in FIG. 5. As can be seen, the level of bFGF is approximately 11 times greater in the detached group than in the non-detached group; the level of TNF-alpha is approximately 8 times greater in the detached group than in the non-detached group; and the level of IL-1 beta is approximately 3 to 4 times greater in the detached group than in the non-detached group.

TABLE 1

Primer Set for real-time PCR.

18rRNA

F1-CAGTGAAACTGCGAATGGCTCATT (SEQ ID NO: 7)
R1-CCCGTCGGCATGTATTAGCTCTAGA (SEQ ID NO: 8)

bFGF

F1-TCTTCCTGCGCATCCATCCAGA (SEQ ID NO: 9)
R1-CAGTGCCACATACCAACTGGAG (SEQ ID NO: 10)

BDNF

F1-CTTGGACAGAGCCAGCGGATTTGT (SEQ ID NO: 11)
R1-CCGTGGACGTTTGCTTCTTTCATG (SEQ ID NO: 12)

NT-3

F1-TCTGCCACGATCTTACAGGTGAACA (SEQ ID NO: 13)
R1-CGCCTGGATCAACTTGATAATGAGG (SEQ ID NO: 14)

NT-4

F1-TACCCTGGCAAGAGAGACGAGGAA (SEQ ID NO: 15)
R1-CCACCGTGCATGGTTTATGATACG (SEQ ID NO: 16)

GDNF

F1-TGCCCTTCGCGCTGACCAGTGACA (SEQ ID NO: 17)
R1-TTCGAGGAAGTGCCGCCGCTTGTT (SEQ ID NO: 18)

IGF-1

F1-TTCAGTTCGTGTGTGGACCAAGG (SEQ ID NO: 19)
R1-GCTTCAGCGGAGCACAGTACATCT (SEQ ID NO: 20)

HGF

F1-AGATGAGTGTGCCAACAGGTGCAT (SEQ ID NO: 21)
R1-AGGTCAAATTCATGGCCAAACCC (SEQ ID NO: 22)

PDGFA

F1-CACTGTTAAGCATGTGCCGGAGAA (SEQ ID NO: 23)
R1-CCAGATCAAGAAGTTGGCCGATGT (SEQ ID NO: 24)

PDGFB

F1-CTTGAACATGACCCGAGCACATTCT (SEQ ID NO: 25)
R1-ATCGATGAGGTTCCGCGAGATCT (SEQ ID NO: 26)

TNF-alpha

F1-CCCAGACCCTCACACTCAGATCAT (SEQ ID NO: 27)
R1-GCAGCCTTGTCCCTTGAAGAGAA (SEQ ID NO: 28)

IL-1 beta

F1-TCAGGAAGGCAGTGTCACTCATTG (SEQ ID NO: 29)
R1-ACACACTAGCAGGTCGTCATCATC (SEQ ID NO: 30)

TGFbeta2

F1-AATGGCTCTCCTTCGACGTGACA (SEQ ID NO: 31)
R1-CCTCCAGCTCTTGGCTCTTATTTGG (SEQ ID NO: 32)

CNTF

F1-GCCGTTCTATCTGGCTAGCAAGGA (SEQ ID NO: 33)
R1-GCCTCAGTCATCTCACTCCAACGA (SEQ ID NO: 34)

MCP-1

F1-ATGCAGGTCTCTGTCACGCTTCTG (SEQ ID NO: 35)
R1-GACACCTGCTGCTGGTGATTCTCTT (SEQ ID NO: 36)

TABLE 1-continued

Primer Set for real-time PCR.

VEGF

| | |
|---|---|
| F1-TCTTCCAGGAGTACCCCGATGAGA | (SEQ ID NO: 37) |
| R1-GGTTTGATCCGCATGATCTGCAT | (SEQ ID NO: 38) |

Angiopoietin-1

| | |
|---|---|
| F1-GCCCAGATACAACAGAATGCGGTT | (SEQ ID NO: 39) |
| R1-CTCCAGCAGTTGGATTTCAAGACG | (SEQ ID NO: 40) |

Angiopoietin-2

| | |
|---|---|
| F1-CTCGGAAACTGACTGATGTGGAAGC | (SEQ ID NO: 41) |
| R1-TGTCCTCCATGTCCAGCACTTTCTT | (SEQ ID NO: 42) |

CTGF

| | |
|---|---|
| F1-ACCCAACTATGATGCGAGCCAACT | (SEQ ID NO: 43) |
| R1-AATTTTAGGCGTCCGGATGCACT | (SEQ ID NO: 44) |

PEDF

| | |
|---|---|
| F2-GCTGTTTCCAACTTCGGCTACGAT | (SEQ ID NO: 45) |
| R2-AGAGAGCCCGGTGAATGACAGACT | (SEQ ID NO: 46) |

Example 4

Characterization of Cytokine Response in Experimental Retinal Detachment

This example characterizes the molecular and cellular responses that occur after retinal detachment by quantifying growth factors, cytokines, and chemokines in a rat model of experimental retinal detachment.

Initial experiments characterized cytokine, chemokine, and growth factor responses to retinal detachment by determining changes in gene expression in the whole neural retina following retinal detachment using 19 different PCR primer sets. An identified subset of cytokines and growth factors was further investigated to determine the cellular origin and time course of gene expression by combining laser capture microdissection (LCM) with quantitative real-time PCR (QPCR), and by immunohistochemistry. LCM allows capture of specific cells in a histological section using laser irradiation (see, for example, Sgroi et al. (1999) CANCER RES. 59: 5656-61). Real-time PCR detects small changes in gene expression using PCR amplification and quantification of mRNA levels with the 2(-Delta Delta C(T)) method (Livak et al. (2001) METHODS. 25: 402-8). In order to pinpoint cellular sources of cytokine production, LCM and QPCR techniques were combined to isolate cells from various retinal layers and quantify the mRNA in those layers. Data from these techniques demonstrates a relationship between retinal detachment, cytokine activation and photoreceptor cell death. Additionally, for certain cytokines and growth factors, protein levels after retinal detachment were examined.

Methods

Retinal detachment was induced by subretinal injection of sodium hyaluronate. Retinal tissues were collected at various time points (1, 3, 6, 24, 72 hours) after inducing retinal detachment. Neural retina was homogenized, and mRNA expression was quantified by QPCR. To identify the cellular sources of expressed genes, samples from various retinal layers were obtained using LCM. Immunohistochemistry and Enzyme Linked-Immuno-Sorbent Assay (ELISA) were performed to show expressional changes of proteins. TUNEL staining was used in order to assess photoreceptor death induced by retinal detachment with or without subretinal administration of cytokines.

Retinal Detachment Procedure

Fifty-five adult male Brown Norway rats (200-300 g, Charles River, Boston, Mass.) were used in this study. Rats were anesthetized with a 1:1 mixture of ketamine (100 mg/mL) and xylazine (20 mg/mL; both from Phoenix Pharmaceutical, St. Joseph, Mo.). Pupils were dilated with a topically applied mixture of phenylephrine (5.0%) and tropicamide (0.8%; Massachusetts Eye and Ear Infirmary internal formulary preparation). A sclerotomy was created approximately 2 mm posterior to the limbus with a 22-gauge needle. Care was taken not to damage the lens during creation of the sclerotomy. A Glaser subretinal injector (20-gauge shaft with a 32-gauge tip, BD Biosciences, San Jose, Calif.) connected to a syringe filled with 10 mg/mL Healon® sodium hyaluronate (Pharmacia and Upjohn Co., Kalamazoo, Mich.) was then introduced into the vitreous cavity. A retinotomy was created in the peripheral retina with the tip of the subretinal injector, and the sodium hyaluronate was slowly injected into the subretinal space, causing detachment of one half of the retina.

Retinal detachments were created only in the right eye of each animal, with the left eye serving as a control. At specified days after retinal detachment, rats were sacrificed with an overdose of sodium pentobarbital, and the eyes were enucleated. Each neural retina was immersed and dissected in cooled PBS and was frozen immediately with dry ice. Samples were kept at −80° C. until used in further experiments.

RNA Extraction and RT-PCR Examination

Total RNA was extracted with a Micro-to-Midi™ Total RNA Purification System (Invitrogen Corp., Carlsbad, Calif.) according to the manufacturer's instructions. Each retina was homogenized manually with 600 µl of RNA lysis solution and added to an equivalent volume of 70% ethanol. The mixture was applied to an RNA spin cartridge and centrifuged at 12,000×g for 15 seconds at 25° C. The cartridge was washed once with wash buffer I and twice with wash buffer II. Total RNA was eluted using 30 µl of RNase-free water. To prevent contamination of genomic DNA, DNase I (Invitrogen Corp., Carlsbad, Calif.) was added, followed by a 15 minute incubation at room temperature. Total RNA concentration was measured using a UV spectrophotometer (UV-1201, Shimadzu corp., Kyoto, JAPAN). Three micrograms of total RNA was used in a reverse transcription reaction using the SuperScript™ III First-Strand Synthesis System for RT-PCR (Invitrogen, Carlsbad, Calif.). First-strand cDNA was amplified using an ABI7700 real-time PCR system with a SYBR® green PCR core kit (Applied Biosystems, Foster City, Calif.) and the PCR primer sets listed in Table 1.

PCR amplification was performed for 40 cycles with two-step PCR methods. Denaturation was at 96° C. for 30 seconds and annealing and extension were at 60° C. for 90 seconds. The quality of the PCR products was evaluated by agarose gel electrophoresis and staining with ethidium bromide. For relative comparison of each gene, the Ct value of real-time PCR data was analyzed with the 2(-Delta Delta C(T)) method (Livak et al. (2001) METHODS. 25: 402-8). To normalize the amount of sample cDNA added to each reaction, the Ct value of each target gene was subtracted by the Ct value of endogenous control (18 rRNA).

Laser Capture Microdissection (LCM)

Three days after retinal detachment, eyes were enucleated and embedded in Tissue-Tek® OCT™ compound (Sakura Finetechnical Co., Ltd., Tokyo, Japan). Transverse cryosections measuring 12 microns and including the optic nerve were made with a cryostat (Micron, Germany) and mounted on Superfrost® Plus slides (Fisherbrand, Pittsburgh, Pa.). Before LCM, sections were dehydrated using 75% ethanol, DEPC water twice, 75% ethanol, 95% ethanol, and 100% ethanol for one minute each and Xylen for 5 minutes.

Tissue separation with LCM was achieved using a laser at 70 mW laser power for 0.75 seconds with a spot size of 7.5 µm for the GCL and for the RPE. These settings were changed to 90 mW for 1.2 seconds with a 15 µm spot size for the INL and for the ONL. LCM was performed on each nuclear layer (GCL, INL, ONL, RPE) from 16 sections in the area of the detached retina and from the corresponding area of the undetached, left eye. Samples collected from cell layers of the left, intact eye served as controls. After collection of aimed cells with the LCM caps (Arcturus, Mountain View, Calif.), total RNA was extracted with a PicoPure™ RNA Isolation Kit (Arcturus, cat# KIT0202) according to the manufacturer's instructions with the recommended optional DNase treatment (Qiagen, catalog#79254, Valencia, Calif.). Total RNA was eluted with 30 µl of Elution Buffer. Subsequently, 24 µl of the solution containing total RNA was used for QPCR.

ELISA of TNF-alpha, IL-1 beta, and MCP-1

Samples of neural retina were collected at 6 and 72 hours after retinal detachment. For each retina, protein was extracted with 200 µl of RIPA lysis buffer (50 mM Tris [pH 8.0], 1% NP-40, 0.5% sodium deoxycholate, 0.1% SDS, 150 mM NaCl) containing one tablet of protease inhibitor cocktail (Complete, Roche Diagnostics, Alameda, Calif.) and was sonicated at 10 watts using a Branson Sonifier® 250 (Branson Ultrasonics Corp., Danbury, Conn.) for 2 seconds. A 30 minute incubation on ice followed. The supernatant was collected after centrifugation at 14,000×g (Micromax RF, Thermo IEC, Needham Heights, Mass.) for 30 minutes at 4° C., and the total protein concentration was measured with a DC protein assay kit (Bio-Rad, Hercules, Calif.). One hundred micrograms of total protein were used for ELISA (Biosource, Camarillo, Calif.), and ELISA was performed according to the protocol that was provided with the kit. The absorbance at 450 nm wavelength was measured using a 96-well plate-reading spectrophotometer (Spectramax 190, Molecular Devices, Sunnyvale Calif.).

Immunohistochemistry

Isolated retinas were fixed in 4% paraformaldehyde (PFA) at 4° C. overnight and then cryoprotected with PBS (0.1 M phosphate buffer [pH, 7.4], 0.15 M NaCl) containing 20% sucrose. Retinal specimens were frozen in Tissue-Tek® OCT™ compound, and 10 µm sections were prepared with a cryostat to include the optic nerve. Sections were mounted onto Superfrost® slides, placed in blocking buffer (PBS containing 10% goat serum, 0.5% gelatin, 3% BSA, and 0.2% Tween20), and incubated with rabbit anti-rat polyclonal bFGF (Santa Cruz Biotech. Inc., Santa Cruz, Calif., 1:200), rabbit anti-rat polyclonal TNF-alpha (1:200), rabbit anti-rat polyclonal IL-1 beta (Pierce Biotechnology, Inc., Rockford, Ill., 1:200) or rabbit anti-rat polyclonal MCP-1 (Peprotec, Rocky Hill, N.J., 1:200). For double staining, mouse monoclonal antibody against glial fibrillary acidic protein (GFAP, Sigma-Aldrich, 1:400), as a marker of astrocytes, or mouse monoclonal antibody against glutamine synthetase (BD Biosciences, San Jose, Calif., 1:200), as a marker of Müller cells, were used. The same procedure was used for the negative control but without the primary antibody. Sections were then incubated with fluorescence-conjugated secondary antibody, either goat anti-mouse immunoglobulin G (IgG) conjugated to Alexa Fluor 488 (green color) or anti-rabbit IgG conjugated to Alexa Fluor 546 (red color) (Molecular Probes, Eugene, Oreg.). Sections were mounted with Vectashield mounting media with propidium iodide (Vector Laboratories, Burlingame, Calif.). Photomicrographs of retinal sections were taken 2 mm from the center of the optic nerve head using fluorescent microscopy (DMRXA camera, Leica, Germany) and OpenLab software, version 2.2.5 (Improvision Inc., Lexington, Mass.).

TUNEL Staining

Subretinal administration of select cytokines was performed following the creation of retinal detachment. Twenty four hours after retinal detachment and subretinal administration of 5 µl of PBS, rat recombinant TNF-alpha (0.1 µg/µl), rat recombinant IL-1 beta (0.1 µg/µl), or rat recombinant MCP-1 (0.1 µg/µl), the eyes were harvested, fixed overnight with 4% PFA, and cryoprotected with 20% sucrose. TUNEL staining was performed using the ApopTag® Fluorescein In Situ Apoptosis detection kit (S7110, Chemicon International, Inc., Temecula, Calif.). The center of the retinal detachment lesion was photographed. TUNEL-positive cells were counted in a masked fashion, and standard error was determined.

Statistics

Data from the experimental and control groups were analyzed with an unpaired T-test using StatView 4.11J software for a Macintosh computer (Abacus concepts Inc., Berkeley, Calif.). The significance level was set to $P<0.05$ (*). Except where otherwise noted, values were expressed as mean±standard deviation (SD).

Results

Significant increases in bFGF, TNF-alpha, IL-1 beta, and MCP-1 mRNA were observed in neural retina 72 hours after retinal detachment. LCM revealed increased expression of mRNA for bFGF and MCP-1 in all retinal layers, with bFGF especially evident in the ONL and MCP-1 evident in the INL. TNF-alpha mRNA was significantly increased in ONL and INL. IL-1 beta mRNA was significantly increased in GCL.

Time course experiments showed that bFGF mRNA was increased after 24 hours and that MCP-1 mRNA was detectable after 1 hour. However, the curve of time dependent increase for MCP-1 mRNA was similar to that of bFGF mRNA. TNF-alpha and IL-1 beta mRNA were increased within 1 hour following retinal detachment; however, TNF-alpha mRNA showed a second increase after 6 hours. ELISA analysis revealed that TNF-alpha, IL-1 beta, and MCP-1 proteins were increased significantly at 6 hours after retinal detachment. Immunohistochemistry indicated bFGF and TNF-alpha protein expression in the whole retina, while IL-1 beta protein was specifically expressed in the astrocytes and MCP-1 protein was expressed in the Müller cells. Subretinal administration of exogenous MCP-1 protein increased TUNEL-positive cells in ONL 24 hours after retinal detachment.

Gene-Expression Following Retinal Detachment

Retinal detachment was induced in the rats, and the expression of 19 different genes was examined by QPCR at 72 hours following detachment. The nineteen genes that were examined included bFGF; brain-derived neurotrophic factor (BDNF); neurotrophin-3,4 (NT-3,4); glial cell line-derived neurotrophic factor (GDNP); insulin growth factor-1 (IGF-1); hepatocyte growth factor (HGF); platelet-derived growth factor A,B (PDGFA,B); TNF-alpha; IL-1 beta; transforming growth factor beta 2 (TGF-beta2); ciliary neurotrophic factor (CNTF); MCP-1; vascular endothelial growth factor (VEGF); angiopoietin-1,2 (Angio-1,2); connective tissue growth factor (CTGF): and PEDF.

Figure 6:
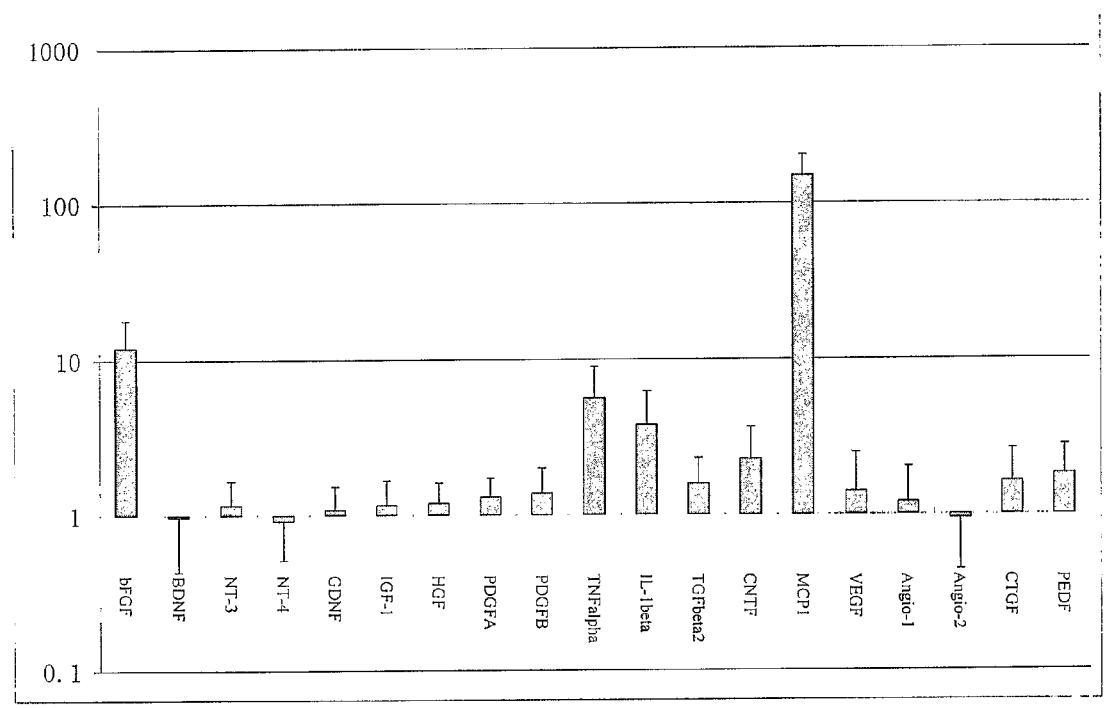
FIG. 6 depicts a bar chart showing retinal mRNA expressional changes for nineteen genes in detached retina versus non-detached retina at 72 hours post detachment.
Figure 7:
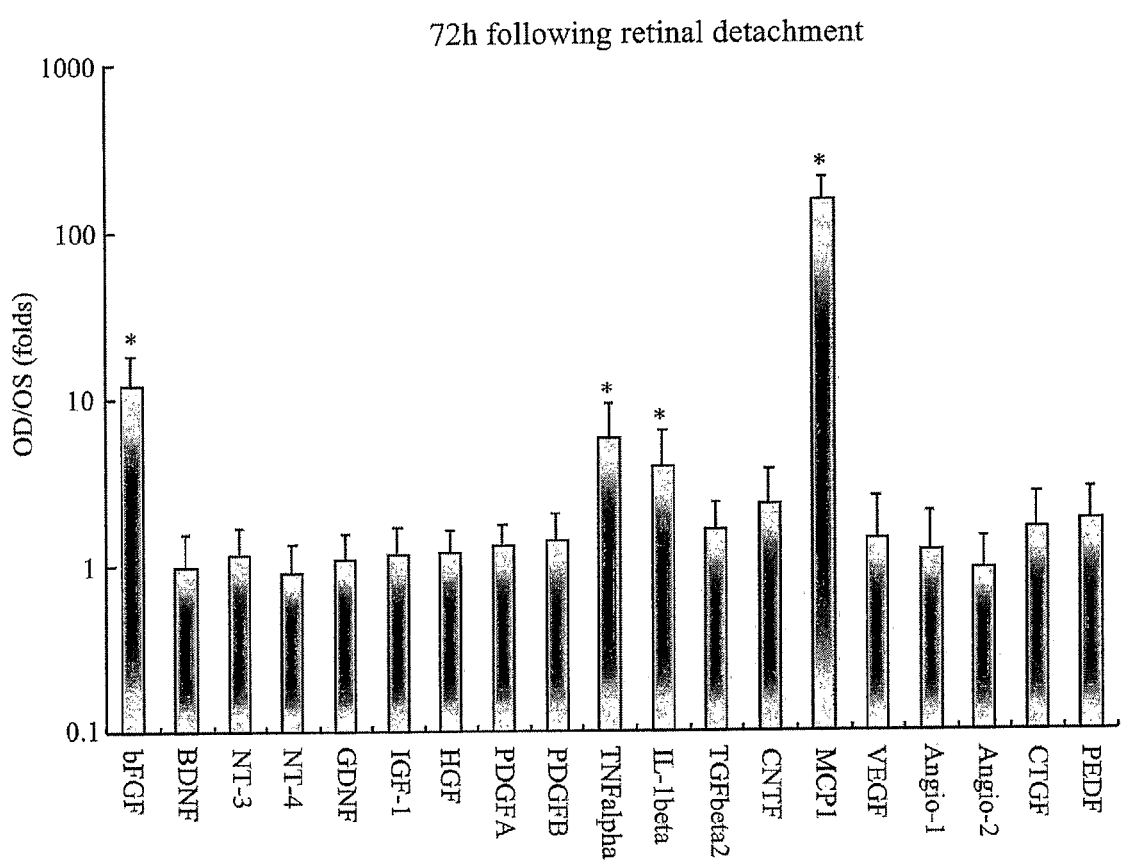
FIG. 7 depicts a bar chart showing retinal mRNA expressional changes for nineteen genes in detached retina of the right eye, or oculus dexter (OD), versus non-detached retina of the left eye, or oculus sinister (OS), at 72 hours post detachment.

FIG. 7, which displays certain data also shown in FIG. 6, indicates the expression pattern of these nineteen genes and shows the average fold increase in expression of each gene's mRNA in detached retinas of right eyes (OD) as compared to the expression of the same gene's mRNA in undetached retinas of left eyes (OS), for six rats. The genes are shown on the x-axis and the average fold increase is shown on the y-axis. The average fold increase in mRNA expression of bFGF (11.6±6.0, $p<0.0001$), TNF-alpha (5.7±3.3, $p=0.0015$), IL-1 beta (3.8±2.5, $p=0.0003$), and MCP-1 (149.3±53.3, $p<0.0001$) was significant at 72 hours following retinal detachment. Other cytokines and growth factors showed no significant change in the average fold increase in expression in the detached retinas in right eyes (OD) versus the non-detached retinas in left eyes (OS).

LCM Analysis

QPCR analysis was performed on samples collected from various retinal layers using LCM. The RPE contains retinal pigment epithelial cells; the ONL primarily contains photoreceptors; the INL is composed of multiple cell types including amacrine cells, bipolar cells, horizontal cells, and Müller cells, whose cellular processes span the retina; and the GCL primarily contains retinal ganglion cells (RGC), displaced amacrine cells, and, to some extent, astrocytes and endothelial cells.

Figure 8:
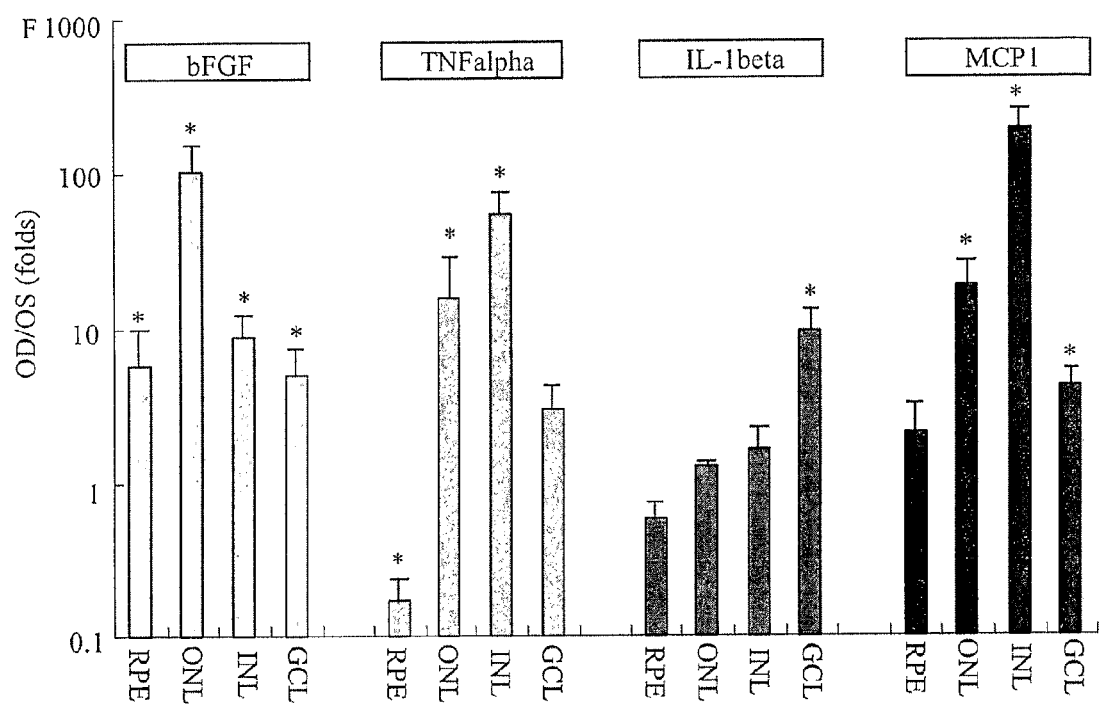
FIG. 8 depicts a bar chart showing mRNA expressional changes in the retinal pigment layer (RPE), the outer nuclear layer (ONL), the inner nuclear layer (INL) and the ganglion cell layer (GCL) of the retina, for each of four genes (bFGF, TNF-alpha, IL-1 beta, and MCP-1), in detached retina versus non-detached retina at 72 hours post detachment.

FIG. 8 shows results of QPCR analysis on LCM-collected samples of three to five rats. The average fold increase in mRNA expression of bFGF was significantly increased in all layers. The average fold increase in mRNA expression of TNF-alpha was significantly decreased in the RPE (0.2±0.1, $p=0.0185$), and increased in the ONL (15.6±12.8, $p=0.0211$) and in the INL (54.4±20.9, $p=0.0008$), but not significantly changed in the GCL. The average fold increase in mRNA expression of IL-1 beta was significantly increased only in the GCL (9.4±3.5, $p=0.0467$), but not in the other layers. The average fold increase in mRNA expression of MCP-1 was increased significantly in ONL (18.6±8.0, $p=0.0493$), INL (187.0±67.1, $p=0.0104$), and GCL (4.0±1.2, $p=0.0164$), but unchanged in RPE. These data suggest that the distribution of genes induced after retinal detachment is specific to various retinal layers. The highest level of gene induction was, for bFGF, in the ONL, for TNF-alpha and MCP-1 in the INL, and for IL-1 beta in the GCL.

Time Course Evaluation Following Retinal Detachment

Figure 9:
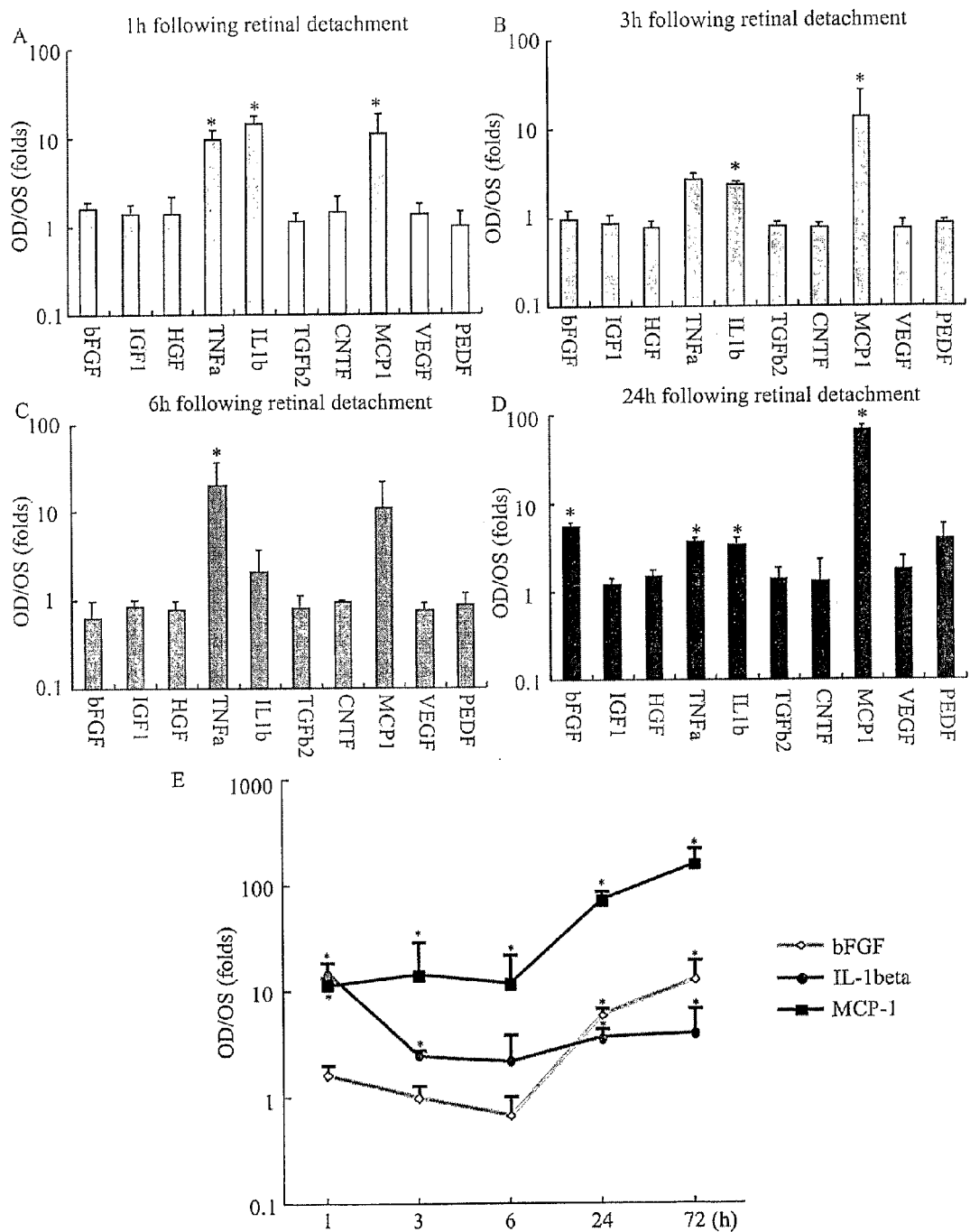
FIGS. 9A-E depict four bar charts and a line graph showing mRNA expressional changes at 1 hour (FIG. 9A), 3 hours (FIG. 9B), 6 hours (FIG. 9C), and 24 hours (FIG. 9D) post retinal detachment, and a time course (FIG. 9E) showing these changes for certain genes.

Three days following retinal detachment, significant average fold increases in mRNA expression were detected for bFGF, TNF-alpha, IL-1 beta, and MCP-1, as shown in FIG. 7. To see earlier time points for these responses, retinal tissues were harvested at 1 h, 3 h, 6 h, and 24 h after induction of detachment. FIGS. 9A-D show the time course evaluation of the average fold increase in mRNA expression in total retina with detachment in right eyes (OD) as compared to total retina without detachment in left eyes (OS) at 1 hour (FIG. 9A), 3 hours (FIG. 9B), 6 hours (FIG. 9C), and 24 hours (FIG. 9D).

As shown in FIG. 9A, at one hour after retinal detachment the average fold increases in mRNA expression of TNF-alpha, IL-1 beta, and MCP-1 were significant. However, MCP-1 mRNA levels were not as elevated at 1 hour compared to 72 hours following retinal detachment (as shown in FIG. 7). The average fold increase of mRNA expression of bFGF was not changed at this time point.

As shown in FIG. 9B, at three hours after retinal detachment the average fold increases of mRNA expression of IL-1 beta and MCP-1 were significant, but the fold increase of IL-1 beta was lower than after 1 hour. The average fold increases of mRNA expression of TNF-alpha and bFGF were not changed significantly.

As shown in FIG. 9C, at six hours after retinal detachment the average fold increase of mRNA expression of TNF-alpha was at its peak level, but the average fold increases of mRNA expression of bFGF, IL-1 beta, and MCP-1 were not significantly changed from their 3 hour levels.

As shown in FIG. 9D, at twenty-four hours after retinal detachment the average fold increase of mRNA expression of bFGF increased significantly. The average fold increases in mRNA expression of TNF-alpha, IL-1 beta, and MCP-1 remained significant.

These data indicate that gene expressional changes for TNF-alpha, IL-1 beta, and MCP-1 can be detected as early as one hour following retinal detachment, and that increased expression of bFGF becomes significant by 24 hours after retinal detachment. As FIG. 9E shows, the peak of IL-1 beta induction was 1 hour after retinal detachment. After 3 hours IL-1 beta dropped and then remained constant. TNF-alpha showed relatively heightened levels at 1 hour, dropped at 3 hours, and peaked at 6 hours (FIGS. 9A-C). As shown in FIG. 9E, the curve of MCP-1 induction was similar to that of bFGF, however MCP-1 increased significantly within 1 hour. These data suggest that inducible factors, MCP-1 and bFGF, overlap 24 hours later and that there may be a functional redundancy between these genes.

ELISA of TNF-Alpha, IL-1 Beta, and MCP-1

Figure 10A:
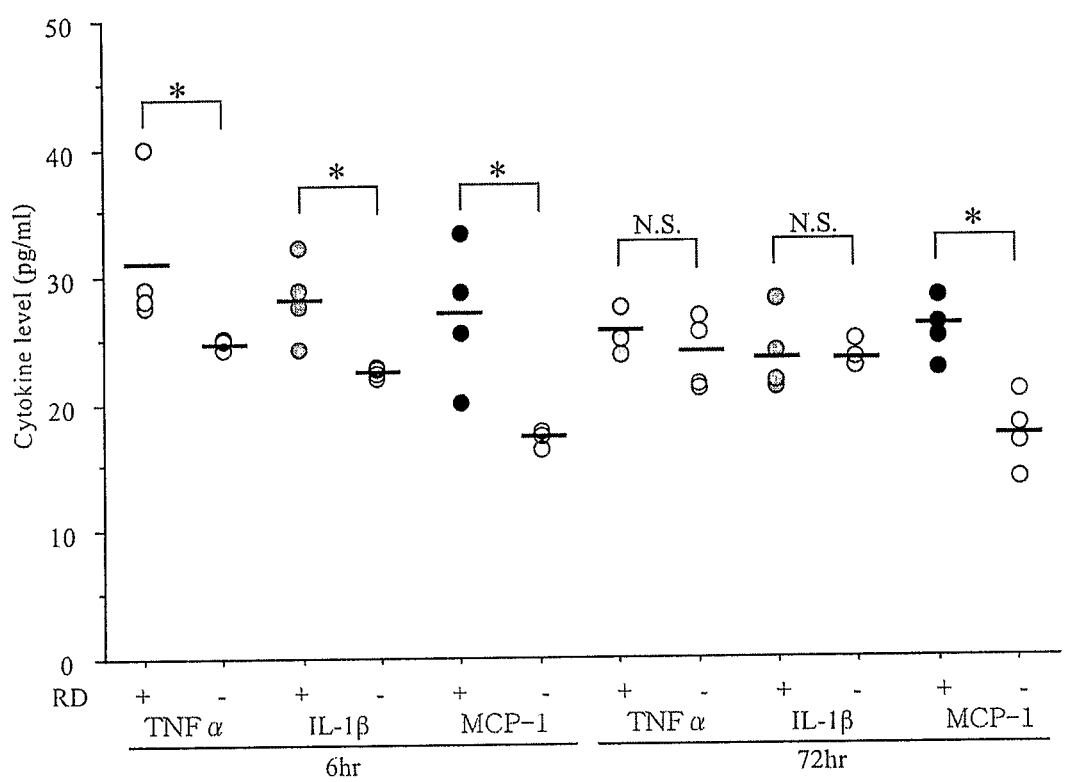
FIG. 10A depicts a plot showing cytokine levels, as determined by ELISA, for TNF-alpha, IL-1 beta, and MCP-1 in detached retinas from right eyes (RD+) and undetached retinas from left eyes (RD−), at 6 and 72 hours post retinal detachment.
Figure 10B:
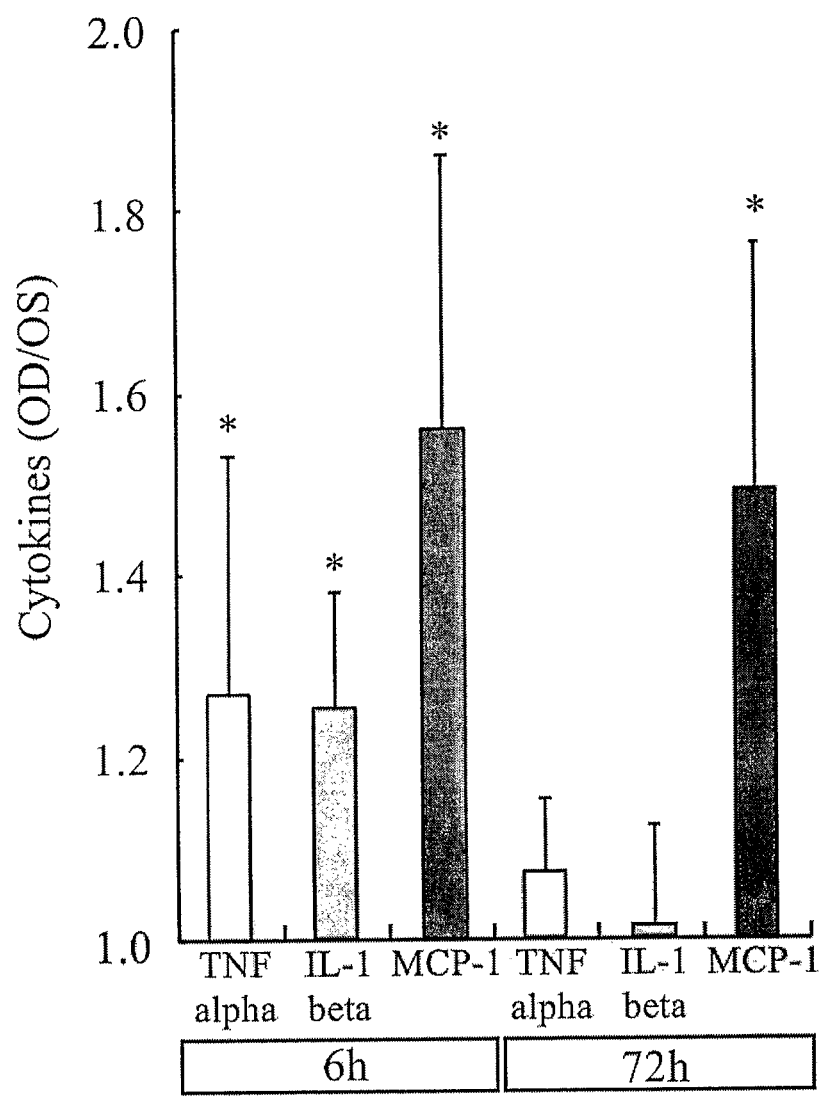
FIG. 10B depicts an alternative view of the data depicted in FIG. 10A, with the y-axis showing the ratio of the average ELISA results for TNF-alpha, IL-1 beta, and MCP-1 in detached retinas from right eyes (OD) versus undetached retinas from left eyes (OS), at 6 and 72 hours post retinal detachment.

To investigate changes in cytokine expression at the protein level, ELISA was performed on neural retina at 6 and 72 hours after retinal detachment. Total protein levels in detached retinas versus undetached retinas did not vary significantly, as shown in Table 2. However, the ratios of TNF-alpha, IL-1 beta, and MCP-1 proteins in the right eye (OD, with detached retina) as compared to the left eye (OS, with non-detached retina) were significantly increased at six hours. Seventy-two hours after retinal detachment, the significant increase in MCP-1 expression was sustained. FIGS. 10A and 10B show the quantitative results of TNF-alpha, IL-1 beta, and MCP-1 protein expression as assessed by ELISA. In FIG. 10A, the y-axis represents measured cytokine levels (mean±SD) in eyes with detached retinas (RD+) and in eyes with undetached retinas (RD−) with statistical significance determined using the Mann-Whitney U test. FIG. 10B shows and alternate view of the same data, in which the y-axis shows the ratio of the average ELISA result from detached retinal samples (OD) versus control retinal samples (OS) at 6 and 72 hours after detachment for 4 rats (n=4, mean±SD). At six hours after retinal detachment in the untreated control left eye, the average concentration of TNF-alpha was 1.24 pg/μg total protein (n=4), IL-1 beta was 1.12 pg/μg total protein, and MCP-1 was 0.87 pg/μg total protein, while in the right eye with retinal detachment, TNF-alpha was 1.57 pg/μg total protein, IL-1 beta was 1.41 pg/μg total protein, and MCP-1 was 1.35 pg/μg total protein. These data indicate that 6 hours after retinal detachment the relative protein levels of TNF-alpha, IL-1 beta, and MCP-1 were significantly increased.

TABLE 2

Total protein per retina of detached retina and control.

|  | RD | RD (−) |  |
|---|---|---|---|
| RD6 h (μg/retina) | 921.5 ± 22.2 | 929.0 ± 46.9 | N.S |
| RD72 h(μg/retina) | 960.3 ± 83.5 | 950.3 ± 38.4 | N.S |

Immunohistochemistry of bFGF, TNF-Alpha, IL-1 Beta and MCP-1 After Retinal Detachment The distribution of bFGF, TNF-alpha, IL-1 beta, and MCP-1 proteins was analyzed at 6 and 72 hours after retinal detachment by immunohistochemistry using polyclonal antibodies against these proteins. In untreated retinal sections, immunoreactivity of bFGF and TNF-alpha was weakly detectable in the entire retina; immunoreactivity of IL-1 beta was distributed in the vitreal surfaces of the GCL; and MCP-1 was slightly detectable in the cell bodies in the GCL and INL.

Six hours following retinal detachment, immunoreactivity of bFGF was unchanged. But after 72 hours, the immunoreactivity of bFGF was increased in the ONL, INL, and GCL, and especially in the vitreal surfaces of the GCL and in the middle row of the INL (Müller cells). Monocytes localized on the outer segment of photoreceptors, which appeared at 72 hours after retinal detachment, also showed immunoreactivity for bFGF.

TNF-alpha was increased in the ONL and INL at 6 hours after retinal detachment, but, by 72 hours, the intensity of the signal was decreased. The infiltrating monocytes showed TNF-alpha immunoreactivity at 72 hours after retinal detachment.

IL-1 beta immunoreactivity was significantly increased in the GCL 6 hours and 72 hours after retinal detachment. However, the signal after 6 hours was stronger than at 72 hours, and monocytes in the subretinal space were not stained. Double labeling with antibody against GFAP, an astrocyte marker, demonstrated that the IL-1 beta immunoreactivity co-localized with astrocytes.

Immunoreactivity for MCP-1 was significantly increased in the INL, with the appearance of spindle-shaped cells that are indicative of Müller cells, by 6 hours. Greater staining was observed at 72 hours. The subretinal monocytes also expressed the MCP-1 protein. The expression of MCP-1 in the INL was co-localized with glutamine synthetase, a Müller cell marker.

These data suggested that bFGF and TNF-alpha were increased in the whole retina, while IL-1 beta and MCP-1 were specifically increased in astrocyte or Müller cells, respectively, in the neural retina.

Figure 11A:
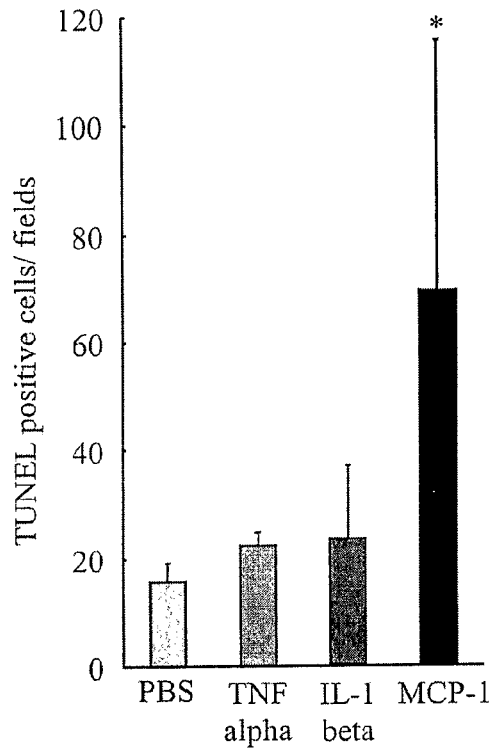
FIG. 11A depicts a bar chart showing quantitative results of TdT-dUTP Terminal Nick End-Labeling (TUNEL) staining of detached retina 24 hours after both retinal detachment and subretinal administration of TNF-alpha, IL-1 beta, MCP-1, or control.
Figure 11B:
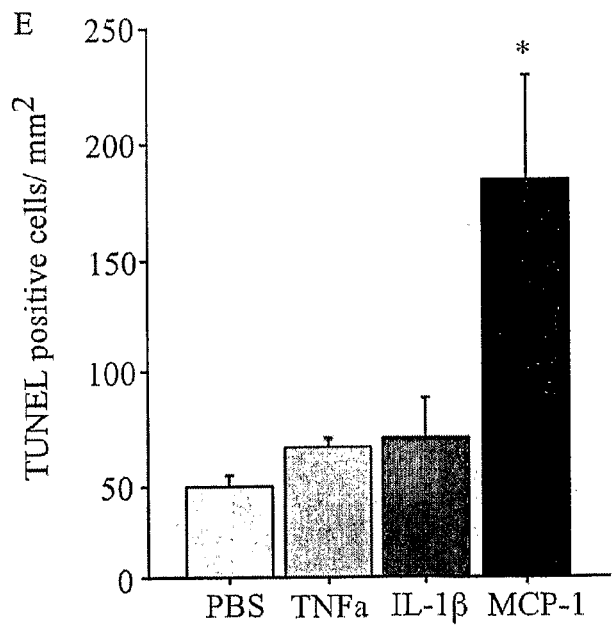
FIG. 11B depicts an alternative view of the data depicted in FIG. 11A, with the y-axis showing TUNEL-positive cells per square millimeter of detached retina 24 hours after both retinal detachment and subretinal administration of TNF-alpha, IL-1 beta, MCP-1, or control.

TUNEL Staining 24 Hours After Retinal Detachment with Subretinal Administration of Cytokines To investigate effects of cytokines on photoreceptor cell death induced by retinal detachment, TUNEL staining was performed 24 hours after retinal detachment with subretinal administration of PBS, TNF-alpha (0.1 μg/μl), IL-1 beta (0.1 μg/μl), or MCP-1 (0.1 μg/μl). FIG. 11A shows the average cell TUNEL-positive cells counted per field, with error bars representing standard error. In the control condition with PBS, TUNEL-positive cells were detected in the ONL 24 hours after retinal detachment (15.3±5.4 cells/field, n=7). The number of TUNEL-positive cells did not change significantly with subretinal administration of TNF-alpha and IL-1 beta. However, subretinal administration of MCP-1 increased the number of TUNEL-positive cells in the ONL 24 hours after retinal detachment (67.7±46.5 cells/field, p=0.0138, n=7). FIG. 11B shows an alternate view of the data shown in FIG. 11A, with the y-axis showing the average cell TUNEL-positive cells counted per square millimeter, with error bars representing standard error. These data suggest that MCP-1 enhances photoreceptor cell death induced by retinal detachment.

Discussion

Experiments described in this example characterized the expressional gene changes of growth factors, cytokines, and chemokines in an animal model of retinal detachment. These experiments showed that mRNAs of TNF-alpha, IL-1 beta, and MCP-1 were detected very early after retinal detachment, and bFGF began to increase at 24 hours. By 72 hours following retinal detachment, bFGF, TNF-alpha, IL-1 beta, and MCP-1 were significantly increased. Examination of the distribution of these genes after retinal detachment using QPCR with samples collected by LCM showed that mRNA of bFGF was most increased in the photoreceptor layer, although the induction was also detected significantly in all other nuclear layers (RPE, INL, GCL). TNF-alpha was increased in the ONL and the INL, and decreased in the RPE. IL-1 beta was specifically increased in the GCL, and MCP-1 was increased in the ONL and the INL.

LCM sampling of cells from the various layers of neural retina correlated with the distribution of bFGF, TNF-alpha, IL-1 beta, and MCP-1 detected by immunohistochemistry. Astrocytes, Müller cells, and subretinal monocytes produced bFGF, TNF-alpha, IL-1 beta, and/or MCP-1 in the retina. Specifically, the immunoreactivity of bFGF and TNF-alpha was increased over the entire neural retina, while IL-1 beta and MCP-1 were increased in the astrocytes or Müller cells, respectively. Subretinal administration of MCP-1 with retinal detachment significantly enhanced the number of TUNEL-positive cells in the ONL 24 hours after retinal detachment, demonstrating that MCP-1 enhances photoreceptor retinal detachment-induced cell death.

The other cytokines and growth factors assessed in the experiments described in this example showed no significant change in the average fold increase in expression of mRNA in the detached retinas in the right eyes (OD) versus the non-detached retinas in the left eyes (OS). Regulation of gene expression of bFGF, TNF-alpha, IL-1 beta, and MCP-1 offers therapeutic avenues to treat retinal detachment and prevent photoreceptor loss, retinal gliosis, and proliferative changes, all of which cause significant vision loss in patients.

Example 5

Neuroprotective Effect of TNF-alpha Suppression Following Retinal Detachment

This example confirms that administration of agents that suppress TNF-alpha, in this case goat TNF-alpha blocking antibody and etanercept, protects against cell death following retinal detachment.

Retinal detachments were experimentally induced in the right eye of Adult Male Norway Brown rats, using the retinal detachment procedure described in Example 4. Retinal detachments were created only in the right eye of each animal, and the left eye served as a control. Following retinal detachment, various treatments were administered subretinally using a Hamilton syringe equipped with a 32-gauge needle. The tip of needle was introduced through a sclerotomy and retinal hole into the subretinal space, and 5 μl of solution, either normal goat serum (0.1 mg/mL), goat anti-TNF-alpha antibody (0.1 mg/mL), or etanercept (2 mg/mL), was injected over 3 minutes. Seventy-two hours after retinal detachment, the eyes were subjected to TUNEL analysis.

Figure 12:
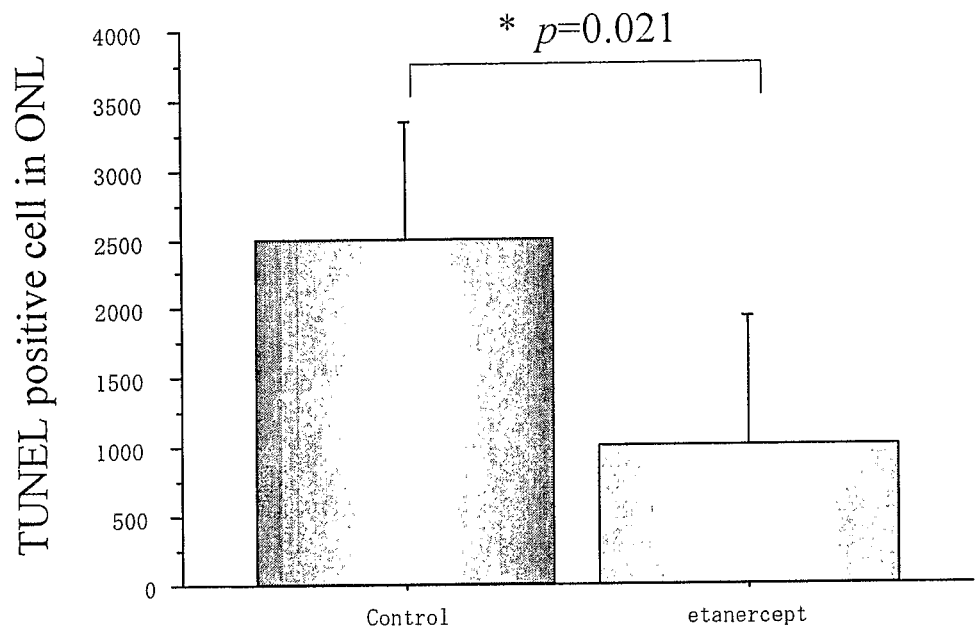
FIG. 12 depicts a bar chart showing quantitative results of TUNEL staining of cells in the ONL of rats with a detached retina 72 hours after retinal detachment and subsequent treatment with etanercept.
Figure 13:
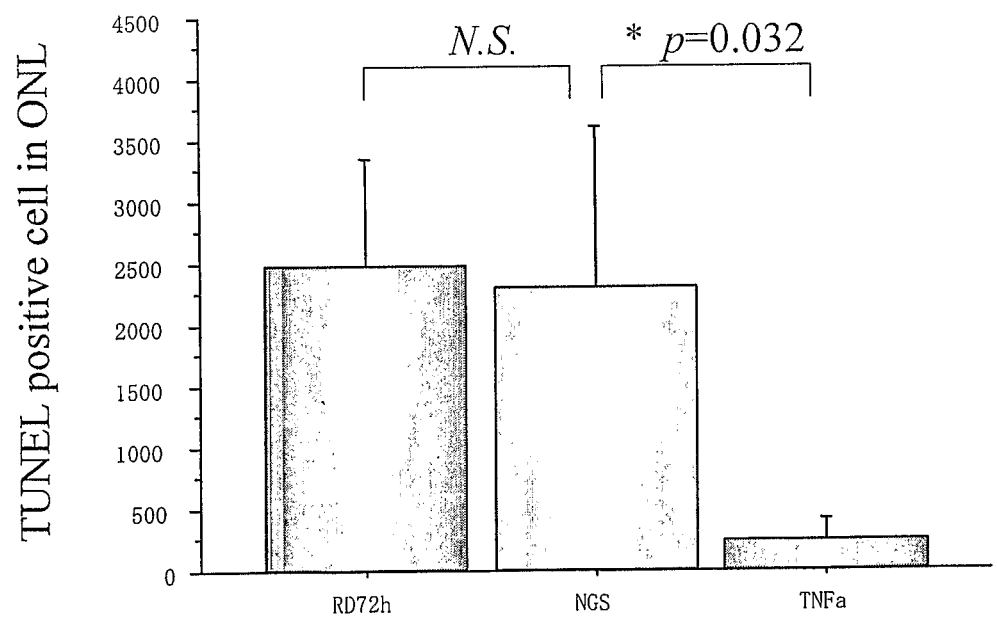
FIG. 13 depicts a bar chart showing quantitative results of TUNEL staining of cells in the ONL of rats with a detached retina 72 hours after retinal detachment and subsequent treatment with either normal goat serum (NGS) or goat anti-TNF-alpha antibody (TNFa)

FIGS. 12 and 13 show TUNEL-positive responses in the ONL at 72 hours following retinal detachment. As shown in FIG. 12, animals treated with etanercept following retinal detachment had a significantly decreased TUNEL-positive response in the ONL at 72 hours as compared to controls. Similarly, FIG. 13 shows that animals treated with goat anti-TNF-alpha antibody (TNFa) following retinal detachment had a significantly decreased TUNEL-positive response in the ONL at 72 hours following retinal detachment as compared to animals treated with normal goat serum (NGS) or controls left untreated (RD72 hours). These data indicate that administration of agents that suppress TNF-alpha, such as goat TNF-alpha blocking antibody or etanercept, protects against photoreceptor cell death following retinal detachment.

Example 6

TNF-alpha, TNF Receptor, and MCP-1 Deficient Animals Show Less Apoptotic Cell Death Following Retinal Detachment This example shows that TNF-alpha deficient mice (TNF−/−), TNF Receptors 1A and 1B double deficient mice (TNFR−/−), and MCP-1 deficient mice exhibit less apoptotic cell death following retinal detachment as compared to wild-type mice.

Knock-out mice deficient in TNF-alpha, TNF Receptors 1A and 1B, or MCP-1 were anesthetized by intraperitoneal injection of a ketamine (62.5 mg/kg) and xylazine (12.5 mg/kg) mixture. For each animal, after dilation of the animal's pupil with 1% cyclopentolate and 2.5% phenylephrine hydrochloride, a scleral puncture was made at the supernasal equator using a glass micropipette. One microliter of vitreous fluid was removed to reduce ocular pressure. Then, a glass micropipette was introduced into the subretinal space, and one microliter of Healon® GV sodium hyaluronate (Pharmacia & Upjohn, Uppsala, Sweden) was injected into the subretinal space. Mice receiving scleral punctures served as a control. At 72 hours after retinal detachment, the eyes were subjected to TUNEL analysis.

Figure 14:
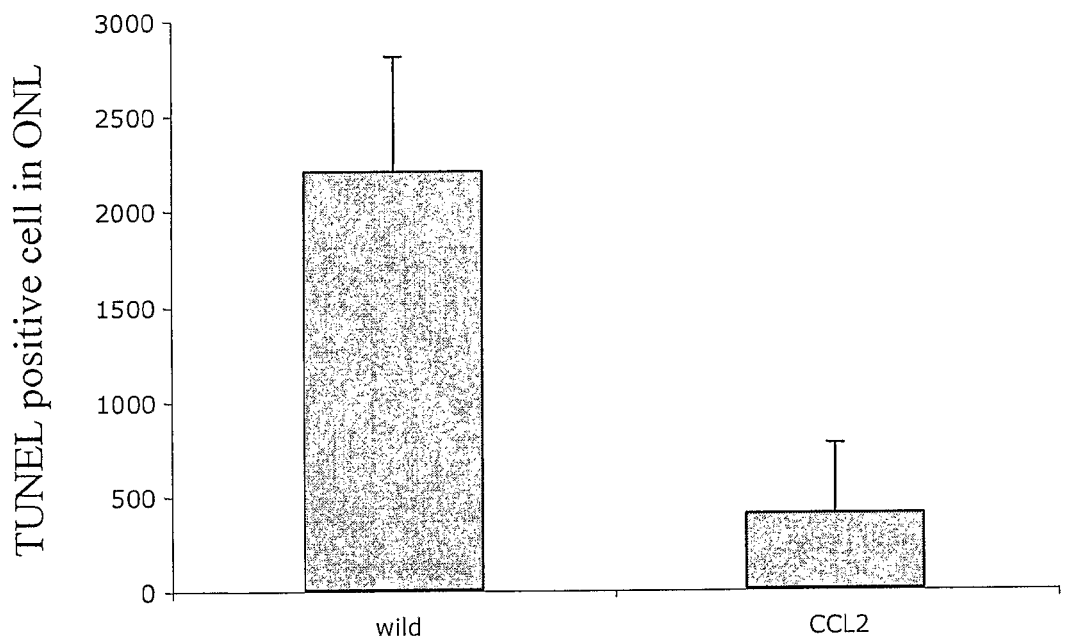
FIG. 14 depicts a bar chart showing quantitative results of TUNEL staining of cells in the ONL of detached retina of either knockout mice lacking the MCP-1 gene (CCL2) or wild-type control mice, 72 hours after retinal detachment.
Figure 15:
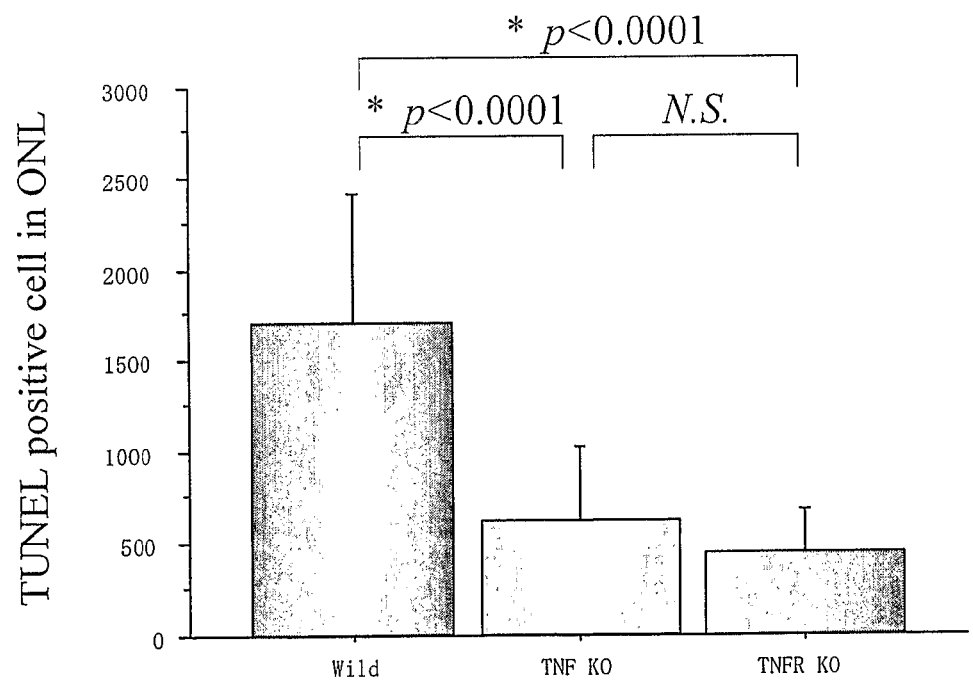
FIG. 15 depicts a bar chart showing quantitative results of TUNEL staining of cells in the ONL of detached retina of either knockout mice deficient in TNF-alpha (TNF KO), knockout mice deficient in TNF Receptors 1A and 1B (TNFR KO), or wild-type control mice 72 hours after retinal detachment.

As shown in FIG. 14, mice deficient in MCP-1 (CCL2) showed less apoptosis than wild-type (wild) mice at 72 hours following retinal detachment. Additionally, as shown in FIG. 15, mice deficient in TNF-alpha (TNF KO) and mice deficient in TNF Receptors 1A and 1B (TNFR KO) showed less apoptosis than wild-type (Wild) mice at 72 hours following retinal detachment. These data further link TNF-alpha, TNF Receptors 1A and 1B, and MCP-1 with apoptosis of photoreceptors and validate them as appropriate treatment targets.

Example 7

Neuroprotective Effect of MCP-1 Suppression Following Retinal Detachment

This example contemplates that administration of agents that suppress MCP-1 protects against cell death following retinal detachment.

Retinal detachments are experimentally induced in the right eye of Adult Male Norway Brown rats, using the retinal detachment procedure described in Example 4. Retinal detachments are created only in the right eye of each animal, and the left eye serves as a control. Following retinal detachment, various treatments are administered subretinally using a Hamilton syringe equipped with a 32-gauge needle. The tip of needle is introduced through a sclerotomy and retinal hole into the subretinal space, and 5 µl of solution containing a suitable concentration of a MCP-1 suppressing agent is injected over 3 minutes.

It is contemplated that treatment with an MCP-1 suppressing agent, including any of those listed herein, following retinal detachment will show decreased TUNEL-positive responses in detached retinas at 72 hours as compared to controls. This indicates that administration of agents that suppress MCP-1 protects against photoreceptor cell death following retinal detachment.

Example 8

Neuroprotective Effect of IL-1 Beta Suppression Following Retinal Detachment

This example contemplates that administration of agents that suppress IL-1 beta protects against cell death following retinal detachment.

Retinal detachments are experimentally induced in the right eye of Adult Male Norway Brown rats, using the retinal detachment procedure described in Example 4. Retinal detachments are created only in the right eye of each animal, and the left eye serves as a control. Following retinal detachment, various treatments are administered subretinally using a Hamilton syringe equipped with a 32-gauge needle. The tip of needle is introduced through a sclerotomy and retinal hole into the subretinal space, and 5 µl of solution containing a suitable concentration of an IL-1 beta suppressing agent is injected over 3 minutes.

It is contemplated that treatment with an IL-1 beta suppressing agent, including any of those listed herein, following retinal detachment will show decreased TUNEL-positive responses in detached retinas at 72 hours as compared to controls. This indicates that administration of agents that suppress IL-1 beta protects against photoreceptor cell death following retinal detachment.

Example 9

Neuroprotective Effect of bFGF Induction Following Retinal Detachment

This example contemplates that administration of agents that induce bFGF protect against cell death following retinal detachment.

Retinal detachments are experimentally induced in the right eye of Adult Male Norway Brown rats, using the retinal detachment procedure described in Example 4. Retinal detachments are created only in the right eye of each animal, and the left eye serves as a control. Following retinal detachment, various treatments are administered subretinally using a Hamilton syringe equipped with a 32-gauge needle. The tip of needle is introduced through a sclerotomy and retinal hole into the subretinal space, and 5 µl of solution containing a suitable concentration of a bFGF inducing agent is injected over 3 minutes.

It is contemplated that treatment with an bFGF inducing agent, including any of those listed herein, following retinal detachment will show decreased TUNEL-positive responses in detached retinas at 72 hours as compared to controls. This indicates that administration of agents that induce bFGF protects against photoreceptor cell death following retinal detachment.

Example 10

Intravitreal Administration of PEDF

This example confirms that an intravitreal administration of PEDF has no significant effect on the mRNA expression of bFGF, TNF-alpha, or IL-1 beta, and fails to significantly protect against photoreceptor cell death following retinal detachment.

In these experiments, retinal detachments were created in Brown Norway rats by injecting 10% hyaluronic acid into the subretinal space using a transvitreous approach. Treatment with PEDF (BioProducts MD, Middletown, Md.) or control vehicle was administered immediately after detachment. In an initial set of experiments, the treatment groups included: intravitreal administration of 2.5 µg PEDF (n=6); intravitreal administration of 5.0 µg PEDF (n=9); subretinal administration of 2.5 µg PEDF (n=6); subretinal administration of 5.0 µg PEDF (n=9); intravitreal administration of control vehicle (n=3); and subretinal administration of control vehicle (n=3). In a second set of experiments, the treatment groups included: intravitreal administration of 5.0 µg PEDF (n=15); subretinal administration of 5.0 µg PEDF (n=15); intravitreal administration of control vehicle (n=9); and subretinal administration of control vehicle (n=9).

For both sets of experiments, all eyes were enucleated 72 hours after retinal detachment and embedded in paraffin. Four micron sections through the area of detachment, including the optic nerve, were obtained. Light microscopy was performed at 3× and at 32× magnification using hematoxylin-eosin staining. TUNEL staining was performed using a commercial kit (Oncogene, San Diego, Calif.) and viewed at 20× magnification using green fluorescein staining for TUNEL and blue DAPI nuclear staining. TUNEL-positive cells were counted per millimeter of tissue by a masked observer. The mean number of TUNEL-positive cells per millimeter of tissue was determined by averaging the number of TUNEL-positive cells per mm of tissue in three sections of each eye. Additionally, a realtime polymerase chain reaction (PCR) was performed for a variety of cytokines, including bFGF, TNF-alpha, and IL-1 beta, on extracted retina from normal eyes (n=6), untreated eyes with retinal detachment (n=6), PEDF-treated eyes with retinal detachment (n=6) and PBS-treated eyes with retinal detachment (n=6).

Light microscopic analysis of detached retinas showed the presence of pyknotic nuclei in the outer nuclear layer, disruption of the normal organization of the photoreceptor outer segments, and loss of photoreceptor nuclei. In the initial set of experiments, TUNEL-staining of detached retina from rats treated with a subretinal injection of control vehicle showed multiple TUNEL-positive cells in the ONL, whereas TUNEL-staining of detached retina from rats treated with a subretinal injection of 5.0 µg PEDF showed fewer TUNEL-positive cells in the ONL. Quantitatively, as shown in Table 3, the initial set of experiments showed that the mean number of TUNEL-positive cells per millimeter of tissue was greater in control eyes with detached retinas having a subretinal sham injection (mean±SD, 63.8±11.9) versus eyes with detached retinas that were subretinally injected with 2.5 µg PEDF (17.6±15.5) or 5.0 µg PEDF (30.4±18.1). These differences were statistically significant by a two-tailed t-test (p=0.007 and p=0.016, respectively). There was no statistically significant difference in the number of TUNEL-positive cells found in the intravitreally-injected control eyes versus the intravitreally-injected PEDF eyes.

TABLE 3

Number of TUNEL-Positive Cells in Initial Set of Experiments.

| Treatment | Mean | SD | P |
|---|---|---|---|
| Intravitreal Control | 23.3 | 11.0 | |
| Intravitreal PEDF 2.5 µg | 16.9 | 14.3 | 0.100 |
| Intravitreal PEDF 5.0 µg | 28.4 | 15.7 | 0.190 |
| Subretinal Control | 63.8 | 11.9 | |
| Subretinal PEDF 2.5 µg | 17.7 | 15.5 | 0.007 |
| Subretinal PEDF 5.0 µg | 30.4 | 18.1 | 0.016 |

However, as shown in Table 4, the second set of experiments conducted with larger numbers of sample and control eyes showed no statistical difference between control eyes with detached retinas having a subretinal sham injection (mean±SD, 38.6±32.2) and eyes with detached retinas that were subretinally injected with 5.0 µg PEDF (35.5±42.1). As with the initial set of experiments, the second set of experiments showed no statistically significant difference in the number of TUNEL-positive cells found in the intravitreally-injected control eyes versus intravitreally-injected PEDF eyes.

TABLE 4

Number of TUNEL-Positive Cells in Second Set of Experiments.

| Treatment | Mean | SD | P |
|---|---|---|---|
| Intravitreal Control | 30.2 | 22.0 | |
| Intravitreal PEDF 5.0 µg | 30.3 | 28.5 | 0.122 |
| Subretinal Control | 38.6 | 32.2 | |
| Subretinal PEDF 5.0 µg | 35.5 | 42.1 | 0.847 |

Figure 16:
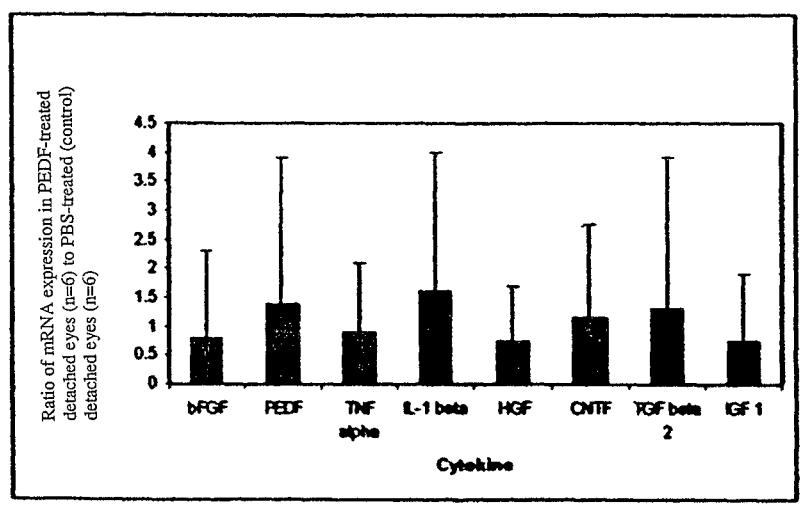
FIG. 16 depicts a bar chart showing retinal mRNA expressional levels in detached retina from rats treated with an intravitreal injection of 5.0 μg pigment epithelium-derived factor (PEDF) versus detached retina from rats treated with an intravitreal injection of PBS control.

A realtime PCR was performed for a variety of cytokines, including bFGF, PEDF, TNF-alpha, IL-1 beta, HGF, CNTF, TGF beta, and IGF 1. The amount of each mRNA from each of six eyes treated with a 5.0 µg intravitreal injection of PEDF just after detachment was averaged. That average was compared with the average amount of mRNA from each of six eyes treated with the PBS control vehicle just after detachment. The results for the intravitreal injection are shown in FIG. 16. As can be seen, intravitreal administration of PEDF does not significantly alter the mRNA levels of bFGF, TNF-alpha, IL-1 beta, or any of the cytokines measured.

Overall, the experiments described in this example show that in a larger sample set, administration of PEDF, either subretinally or intravitreally, has no significant effect on photoreceptor cell death following retinal detachment as measured using TUNEL.

INCORPORATION BY REFERENCE

The entire content of each patent and non-patent document disclosed herein is expressly incorporated herein by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A method of preserving the viability of photoreceptor cells disposed within a retina of a mammalian eye following retinal detachment, the method comprising:

administering to a mammal having an eye in which a region of the retina has been detached an amount of a neuroprotective agent selected from the group consisting of etanercept, an anti-TNF-alpha antibody, and combinations thereof sufficient to preserve the viability of photoreceptor cells disposed within the region of the detached retina.

2. The method of claim 1, wherein the neuroprotective agent is administered to the mammal prior to reattachment of the region of detached retina.

3. The method of claim 1 or 2, wherein the neuroprotective agent is administered to the mammal after reattachment of the region of detached retina.

4. The method of claim 1, wherein the neuroprotective agent is administered locally or systemically.

5. The method of claim 1, wherein a plurality of neuroprotective agents are administered to the mammal.

6. The method of claim 5, wherein the neuroprotective agents are administered locally or systemically.

7. The method of claim 4 or 6, wherein at least one neuroprotective agent is administered by intraocular, intravitreal, or transcleral administration.

8. The method of claim 1, wherein the neuroprotective agent reduces the number of photoreceptor cells in the region that die following retinal detachment.

9. The method of claim 1, wherein the retinal detachment occurs as a result of a retinal tear, retinoblastoma, melanoma, diabetic retinopathy, uveitis, choroidal neovascularization, retinal ischemia, pathologic myopia, or trauma.

10. The method of claim 1, wherein the neuroprotective agent is etanercept.

11. The method of claim 1, wherein the neuroprotective agent is an anti-TNF-alpha antibody.

12. A method of preserving the viability of photoreceptor cells disposed within a retina of a mammalian eye following retinal detachment, the method comprising:

administering to a mammal's retina, the mammal having an eye in which a region of the retina has been detached, an amount of a neuroprotective agent selected from the group consisting of etanercept, an anti-TNF-alpha antibody, and combinations thereof sufficient to preserve the viability of photoreceptor cells disposed within the region of the detached retina.

13. The method of claim 12, wherein at least one neuroprotective agent is administered by intraocular, intravitreal, or transcleral administration.

14. The method of claim 12, wherein the neuroprotective agent is administered to the mammal prior to reattachment of the region of detached retina.

15. The method of claim 12, wherein the neuroprotective agent is administered to the mammal after reattachment of the region of detached retina.

16. The method of claim 12, wherein the retinal detachment occurs as a result of a retinal tear, retinoblastoma, melanoma, diabetic retinopathy, uveitis, choroidal neovascularization, retinal ischemia, pathologic myopia, or trauma.

17. The method of claim 12, wherein the neuroprotective agent is etanercept.

18. The method of claim 12, wherein the neuroprotective agent is an anti-TNF-alpha antibody.

* * * * *